United States Patent [19]

Pierce et al.

[11] Patent Number: 5,824,643
[45] Date of Patent: Oct. 20, 1998

[54] THERAPEUTIC USES OF KERATINOCYTE GROWTH FACTOR

[75] Inventors: Glenn Francis Pierce, Rancho Santa Fe; Regina Mae Housley, Thousand Oaks; Charles Frederick Morris, Newbury Park, all of Calif.

[73] Assignee: Amgen Inc., Thousand Oaks, Calif.

[21] Appl. No.: 482,251

[22] Filed: Jun. 7, 1995

Related U.S. Application Data

[63] Continuation of Ser. No. 312,483, Sep. 26, 1994, abandoned, which is a continuation-in-part of Ser. No. 40,742, Mar. 26, 1993, abandoned.

[51] Int. Cl.$^6$ ........................... C07K 14/91; A61K 38/18
[52] U.S. Cl. .............................................. 514/12; 514/21
[58] Field of Search .......................................... 514/12, 21

[56] References Cited

U.S. PATENT DOCUMENTS

| | | | |
|---|---|---|---|
| 3,917,824 | 11/1975 | Camble et al. | 514/12 |
| 4,820,690 | 4/1989 | Gregory et al. | 514/12 |

FOREIGN PATENT DOCUMENTS

| | | |
|---|---|---|
| 0 298 723 A1 | 1/1989 | European Pat. Off. |
| 0 455 422 A2 | 11/1991 | European Pat. Off. |
| WO 90/08771 | 8/1990 | WIPO |
| 9008771 | 9/1990 | WIPO |
| WO 92/14480 | 9/1992 | WIPO |
| WO 95/01434 | 1/1995 | WIPO |

OTHER PUBLICATIONS

Ago et al., "Crystal Structure of Basic Fibroblast Growth Factor at 1.6 Å Resolution", *J. Biochem.*, 110:360–363 (1991).

Alarid et al., "Keratinocyte Growth Factor Functions in Epithelial Induction During Seminal Vesicle Development", *Proc. Natl. Acad. Sci. USA*, 91:1074–1078 (1994).

Arakawa et al., "Production and Characterization of an Analog of Acidic Growth Factor with Enhanced Stability and Biological Activity", *Protein Engineering*, 6(5):541–546 (1993).

Bottaro et al., "Characterization of the Receptor for Keratinocyte Growth Factor", *The Journal of Biological Chemistry*, 265(22):12767–12770, (1990).

Burgess and Maciag, "The Heparin–binding (Fibroblast) Growth Factor Family of Proteins", *Annu. Rev. Biochem.*, 58:575–606 (1989).

Canatan et al., "Expression of Keratinocyte Growth Factor (KGF) on Normal and Archival Canine Hyperplastic Prostatic Tissues", *FASEB Journal*, 8(4–5):A930, Abstract 5388 (1994).

Chedid et al., "Regulation of Keratinocyte Growth Factor Gene Expression by Interleukin 1", *The Journal of Biological Chemistry*, 269(14):10753–10757 (1994).

Dekowski et al., "Dexamethasone Inhibits Keratinocyte Growth Factor (KGF) mRNA Expression in Human Fetal Lung Transplants", *Pediatric Research*, 35(4 Part 2):65A, Abstract 378 (1994).

Dignass et al., "Fibroblast Growth Factors Modulate Intestinal Epithelial Cell Growth and Migration", *Gastroenterology*, 106(4):A603 (1994).

Dlugosz et al., "KGF Induces TGFa Expression and Activates the EGF Receptor Signalling Pathway to Alter Keratinocyte Growth and Differentiation In Vitro", *Journal of Investigative Dermatology*, 102(4):527, Abstract 24 (1994).

Dlugosz et al., "KGF Induces TGFa Expression and Activates the EGF Receptor to Alter Keratinocyte Growth and Differentiation In Vitro", *Proceedings of the American Association of Cancer Research Annual Meeting*, 35(0):37, Abstract 221 (1994).

Eriksson et al., "Refinement of the Structure of Human Basic Fibroblast Growth Factor at 1.6Å Resolution and Analysis of Presumed Heparin Binding Sites by Selenate Substitution", *Protein Science*, 2:1275–1284 (1993).

Finch et al., "Human KGF Is FGF–Related with Properties of a Paracrine Effector of Epithelial Cell Growth", *Science*, 245:752–755 (1989).

Fusenig et al., "Paracrine Regulation of Keratinocyte Growth and Differentiation by Epithelial–Mesenchymal Interactions", *Supplement O*(18C):273, Abstract PZ022 (1994).

Gimenez–Gallego, et al., "Fibroblast Growth Factors, Proteins with a Broad Spectrum of Biological Activities", *Neurological Research*, 16:313–316 (1994).

Guo et al., "Epidermal Expression of KGF Causes Remarkable Changes In the Skin of Transgenic Mice", *Journal of Cellular Biochemistry, Abstract Supplilemennt 17A*, Abstract BZ642:317 (1993).

Havill et al., "Keratinocyte Growth Factor (rhKGF) Has Hepatic Stimulatory Efffects In Vivo", *FASEB Journal*, 8(4–5)A930, Abstract 5387 (1994).

Hebda et al., "Keratinocyte Growth Factor:Stimulation of Epidermal Regeneration in Partial Thickness Wounds in Pig Skin", *J. Invest. Dermatol.*, 100(4):557, Abstract 414 (1993).

Imagawa et al., "Keratinocyte Growth Factor and Acidic Fibroblast Growth Factor are Mitogens for Primary Cultures of Mammary Epithelium", *Biochem. Biophys. Res. Commun.* (*USA*), 204(3):1165–1169 (1994).

(List continued on next page.)

*Primary Examiner*—Cecilia J. Tsang
*Assistant Examiner*—P. Lynn Touzeau
*Attorney, Agent, or Firm*—Thomas D. Zindrick; Steven M. Odre; Ron K. Levy

[57] ABSTRACT

Based on extensive in vivo studies in animals, it has now been discovered that KGF stimulates proliferation, growth and differentiation in various cells of epithelial tissue, besides keratinocytes. This better understanding of the biological effects of KGF in vivo enables the use of this polypeptide as a therapeutic agent, suitably formulated in a pharmaceutical composition, for the specific treatment of disease states and medical conditions afflicting tissues and organs such as the dermal adnexae, the liver, the lung, and the gastrointestinal tract.

24 Claims, 25 Drawing Sheets

OTHER PUBLICATIONS

Inatomi et al., "Keratinocyte Growth Factor (KGF) Accelerates Corneal Epithelial Wound Healing in Rabbits", *Investigative Ophthalmology & Visual Science*, 35(4):1318, Abstract 299 (1994).

Ishii et al., "Preferential Expression of the Third Immunoglobulin–like Domain of K–sam Product Provides Keratinocyte Growth Factor–dependent Growth in Carcinoma Cell Lines", *Cancer Research*, 54(2):518–522 (1994).

Itoh et al., "Keritinocyte Growth Factor as a Mitogen for Primary Culture of Rat Hepatocytes", *Biochem. Biophys. Res. Commun.*, 192(3):1011–1015 (1993).

Kan et al., "Receptor Phenotype Underlies Differential Response of Hepatocytes and Nonparenchymal Cells to Heparin–binding Fibroblast Growth Factor Type 1 (aFGF) and Type 2 (bFGF)", *In Vitro Cell Dev Biol*, 28A(7–8):515–520 (1992).

Koji et al., "Progesterone–dependent Expression of Keratinocyte Growth Factor mRNA in Stromal Cells of the Primate Endometrium: Keratinocyte Growth Factor asa Progestomedin", *The Journal of Cell Biology*, 125(2):393–401 (1994).

Latkowski et al., "Keratinocyte Growth Factor and Keratin Gene Regulation", *The Journal of Investigative Dermatology*, 102(4):640, Abstract 700 (1994).

Leung et al., "Keratinocyte Growth Factor Enhances Colonic Mucus Production in Normal Rats and Rats Treated with Dextran Sulfate Sodium", *Gastroenterology*, 106(4):A617 (1994).

Marchese et al., "Human Keratinocyte Growth Factor Activity on Proliferation and Differentiation of Human Keratinocytes: Differentiation Response Distinguishes KGF from EGF Family", *Journal of Cellular Physiology*, 144:326–332 (1990).

Mason et al., "FGF–7 (keratinocyte growth factor) Expression During Mouse Development Suggests Roles in Myogenesis, Forebrain Regionalisation and Epithelial–mesenchymal Interactions", *Mechanisms of Development*, 45:15–30 (1994).

McGarvey et al., "Keratinocyte Growth Factor and Receptor Expression in Benign and Malignant Prostate", *Journal of Cellular Biochemistry*, Supplement O(18D):232, Abstract Y117 (1994).

Miki et al., "Expression cDNA Cloning of the KGF Receptor by Creation of a Transforming Autocrine Loop", *Science*, 251:72–75 (1991).

Ohning et al., "Keratinocyte Growth Factor Promotes Healing of Acetic Acid–Induced Gastric Ulcers in Rats", *Gastroenterology*, 106(4 Suppl.):A150 (1994).

Ohning et al., "Kertinocyte Growth Factor Simulates Proliferation and Alters Differentiation of the Gastric Fundic Mucosa in Rats", *Gastroenterology*, 106(4 Suppl):A624 (1994).

Panos et al., "Intratracheal Instillation of Keratinocyte Growth Factor Prevents Hyperoxia–induced Mortality in Rats", *Clinical Research*, 42(3):426A (1994).

Panos et al., "Keratinocyte Growth Factor and Hepatocyte Growth Factor/Scatter Factor are Heparin–binding Growth Factors for Alveolar Type II Cells in Fibroblast–conditioned Medium", *J. of Clin. Invest.*, 92(2):969–977 (1993).

Pekonen et al., "Differential Expression of Keratinocyte Growth Factor and Its Receptor in the Human Uterus", *Molecular and Cellular Endocrinology*, 95:43–49 (1993).

Pierce et al., "Stimulation of All Epithelial Elements during Skin Regeneration by Keratinocyte Growth Factor", *J. Exp. Med.*, 179:831–840 (1994).

Ron et al., "Expression of Biologically Active Recombinant Keratinocyte Growth Factor", *The Journal of Biological Chemistry*, 268(4):2984–2988 (1993).

Rubin et al., "Purification and Characterization of a Newly Identified Growth Factor Specific for Epithelial Cells", *Proc. Natl. Acad. Sci. USA*, 86:802–806 (1989).

Rubin, J.S., "KGF Is A Paracrine Mediator of Epithelial Cell Growth", *Proc. Am. Assoc. Cancer Res. Annual Meeting*, 34(0):588 (1993).

Slayden et al., "Keratinocyte Growth Factor (KGF) and KGF Receptor (KGFR) mRNAs in the Cervix, Placenta, and Decidua of Rhesus Macaques", *Biology of Reproduction*, 59(Suppl.1):121, Abstract 267 (1994).

Sotozono et al., "KGF and KGF Receptor mRNA Expression in Cultured Rabbit Corneal Cells", *Invest. Ophthalmology & Visual Science*, 35(4):1941, Abstract 3170–60 (1994).

Stalano–Coico et al., "Human Keratinocyte Growth Factor Effects in a Porcine Model of Epidermal Wound Healing", *The Journal of Experimental Medicine*, 178(3):865–878 (1993).

Strain et al., "Keratinocyte Growth Factor and Fibroblast Growth Factor Action on DNA Synthesis in Rat and Human Hepatocytes: Modulation by Heparin", *Exp. Cell Research*, 210(2):253–259 (1994).

Tang et al., "Upregulation of Fibroblast Keratinocyte Growth Factor mRNA Expression by Interleukin–1–alpha, Interleukin–1beta and Tumor Necrosis Factor Alpha", *Journal of Investigative Dermatology*, 102(4):528, Abstract 25 (1994).

Tsuboi et al., "Keratinocyte Growth Factor (FGF–7) Stimulates Migration and Plasminogen Activator Activity of Normal Human Keratinocytes", *The Journal of Investigative Dermatology*, 101(1):49–53 (1993).

Tuan et al., "Dermal Fibroblasts Activate Keratinocyte Outgrowth on Collagen Gels", *Journal of Cell Science*, 107(8):2285–2289 (1994).

Ulich et al., "Keratinocyte Growth Factor is a Growth Factor for Type II Pneumocytes In Vivo", *J. Clin. Invest.*, 93(3):1298–1306 (1994).

Ulich et al., "Keratinocyte Growth Factor is a Growth Factor for Mammary Epithelium In Vivo", *Amer. J. of Pathology*, 144(5):862–868 (1994).

Werner et al., "The Function of KGF in Morphogenesis of Epithelium and Reepithelialization of Wounds", *Science*, 266:819–822 (1994).

Werner et al., "Induction of Keratinocyte Growth Factor Expression is Reduced and Delayed During Wound Healing in the Genetically Diabetic Mouse", *J. of Invest. Dermatol.*, 103(4):469–473 (1994).

Werner et al., "Large Induction of Keratinocyte Growth Factor Expression in the Dermis during Wound Healing", *Proc. Natl. Acad. Sci. USA*, 89(15):6896–6900 (1992).

Wilson et al., "EGF, HGF, KGF, and Human Corneal Epithelial Cell Motility, Proliferation, and Differentitation", *Investigative Ophthalmology & Visual Science*, 35(4):1319, Abstract 301 (1994).

Wilson et al., "Hepatocyte Growth Factor (HGF), Keratinocyte Growth Factor (KGF), Their Receptors and the Cells of the Cornea", *The FASEB Journal*, 7(3):A493, Abstract 2857 (1993).

Wu et al., "KGF Accelerates Ischemic Dermal Ulcer Healing in the Rabbit Ear", *Surgical Forum*, 44(O):704–706 (1993).

Yan et al., "Sequence of Rat Keratinocyte Growth Factor (Heparin–binding Growth Facyor Type 7)", *Chemical Abstracts,* 118(15):103, Abstract 140028v (1993).

Yi et al., "Keratinocyte Growth Factor Induces Pancreatic Ductal Epithelial Proliferation", *Amer. Journal of Pathology,* 145(1):80–85 (1994).

Yi et al., "Keratinocyte Growth Factor is a Growth Factor for Type II Pneumocyte In Vivo", *Modern Pathology,* 7(1):156A, Abstract 912 (1994).

Zeeh et al., "Keratinocyte Growth Factor Improves Healing in an Experimental Model of Colitis in Rats", *Gastroenterology,* 106(4 Suppl):A853 (1994).

Zhu et al., "Three–Dimensional Structures of Acidic and Basic Fibroblast Growth Factors", *Science,* 251:90–93 (1991).

Finch et al., Science, vol. 245:pp. 752–755 (1989).

Staiano–Cocio et al., J. Expt Med., vol. 178(3): 865–878 (1993).

```
NdeI                            KGF-dsd
TATGTGCAATGACATGACTCCAGAGCAAATGGCTACAAATGTGAACTGTTCCAGCCCTGA
    ACACGTTACTGTACTGAGGTCTCGTTTACCGATGTTTACACTTGACAAGGTCGGGACT

M  C  N  D  M  T  P  E  Q  M  A  T  N  V  N  C  S  S  P  E-

GCGACACACAAGAAGTTATGATTACATGGAAGGAGGGGATATAAGAGTGAGAAGACTCTT
CGCTGTGTGTTCTTCAATACTAATGTACCTTCCTCCCCTATATTCTCACTCTTCTGAGAA

R  H  T  R  S  Y  D  Y  M  E  G  G  D  I  R  V  R  R  L  F-

KpnI
                |----------------- synthetic DNA ------------
CTGTCGAACACAGTGGTACCTGCGTATCGACAAACGCGGCAAAGTCAAGGGCACCCAAGA
GACAGCTTGTGTCACCATGGACGCATAGCTGTTTGCGCCGTTTCAGTTCCCGTGGGTTCT

C  R  T  Q  W  Y  L  R  I  D  K  R  G  K  V  K  G  T  Q  E-

------------------------------------------------------------
GATGAAAAACAACTACAATATTATGGAAATCCGTACTGTTGCTGTTGGTATCGTTGCAAT
CTACTTTTTGTTGATGTTATAATACCTTTAGGCATGACAACGACAACCATAGCAACGTTA

M  K  N  N  Y  N  I  M  E  I  R  T  V  A  V  G  I  V  A  I-

EcoRI
--------------------|
CAAAGGTGTTGAATCTGAATTCTATCTTGCAATGAACAAGGAAGGAAAACTCTATGCAAA
GTTTCCACAACTTAGACTTAAGATAGAACGTTACTTGTTCCTTCCTTTTGAGATACGTTT

K  G  V  E  S  E  F  Y  L  A  M  N  K  E  G  K  L  Y  A  K-

GAAAGAATGCAATGAAGATTGTAACTTCAAAGAACTAATTCTGGAAAACCATTACAACAC
CTTTCTTACGTTACTTCTAACATTGAAGTTTCTTGATTAAGACCTTTTGGTAATGTTGTG

K  E  C  N  E  D  C  N  F  K  E  L  I  L  E  N  H  Y  N  T-

ATATGCATCAGCTAAATGGACACACAACGGAGGGGAAATGTTTGTTGCCTTAAATCAAAA
TATACGTAGTCGATTTACCTGTGTGTTGCCTCCCCTTTACAAACAACGGAATTTAGTTTT

Y  A  S  A  K  W  T  H  N  G  G  E  M  F  V  A  L  N  Q  K-

GGGGATTCCTGTAAGAGGAAAAAAAACGAAGAAAGAACAAAAAACAGCCCACTTTCTTCC
CCCCTAAGGACATTCTCCTTTTTTTTGCTTCTTTCTTGTTTTTTGTCGGGTGAAAGAAGG

G  I  P  V  R  G  K  K  T  K  K  E  Q  K  T  A  H  F  L  P-

TATGGCAATAACTTAATAG
ATACCGTTATTGAATTATCCTAG

M  A  I  T  *       BamHI
```

FIG. 1

FIG.5A
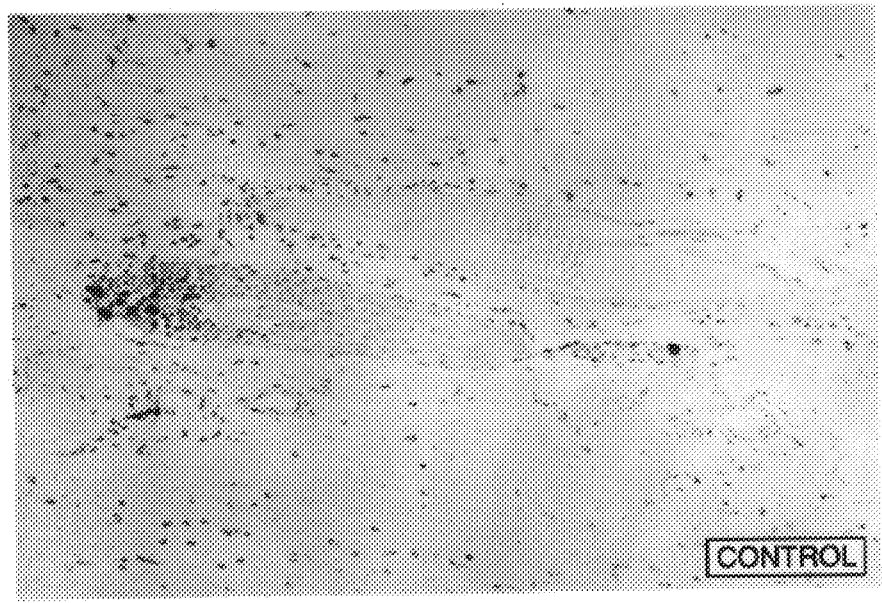
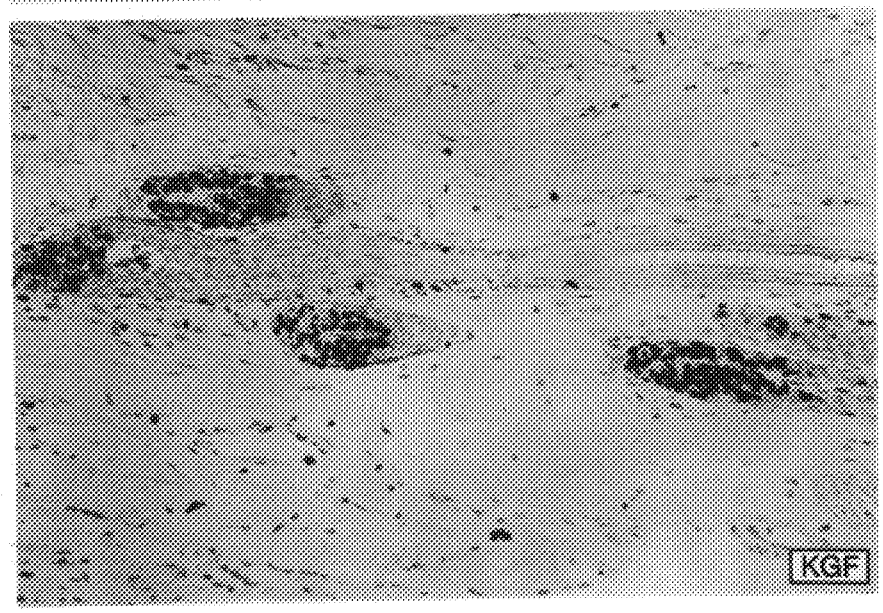
FIG.5B

FIG.6A
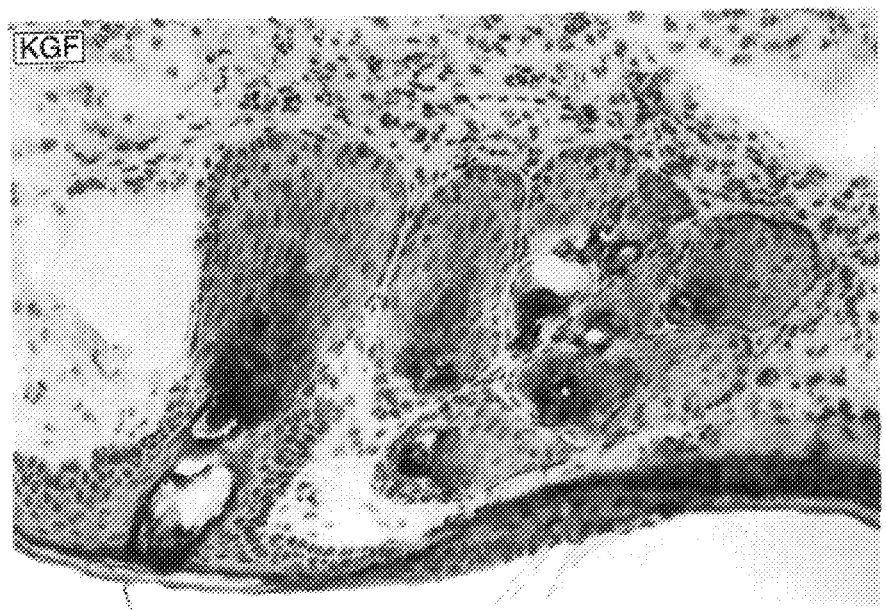
FIG.6B

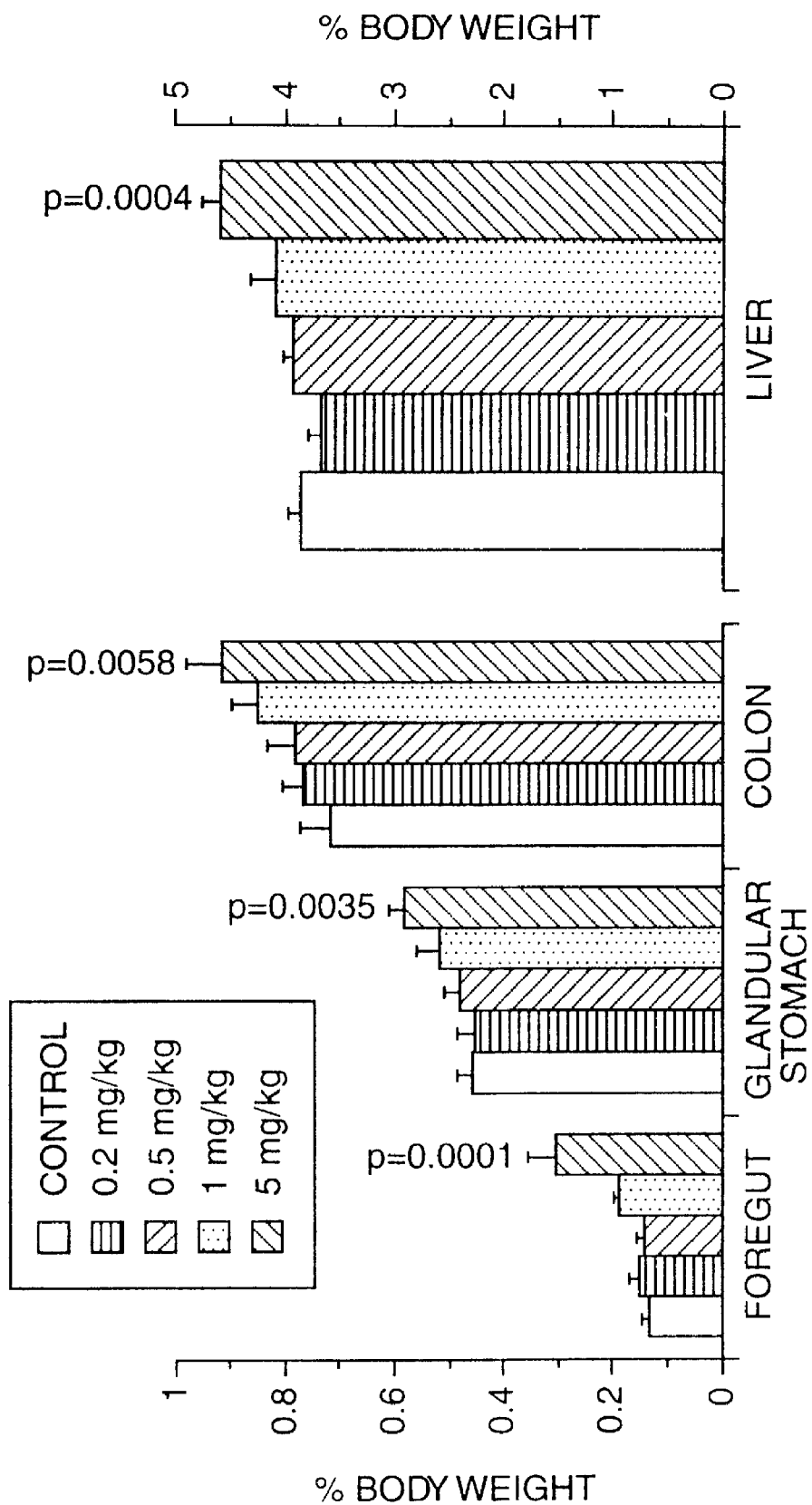

THERAPEUTIC USES OF KERATINOCYTE GROWTH FACTOR

This application is a continuation, of application Ser. No. 08/312,483, filed Sep. 26, 1994, now abandoned, which is a continuation-in-part of application Ser. No. 08/040,742, filed Mar. 26, 1993, now abandoned, which is hereby incorporated by reference.

FIELD OF THE INVENTION

The present invention relates to the application of keratinocyte growth factor (KGF) to stimulate the proliferation, growth and differentiation of cells other than keratinocytes, and to the administration of KGF to patients where these biological effects are useful to regenerate damaged or diseased cells and tissues.

BACKGROUND OF THE INVENTION

In recent years advances in biotechnology have led to the development and therapeutic use of novel recombinant polypeptides, including erythropoietin and granulocyte colony stimulating factor, to the benefit of many human patients. Increasing numbers of other polypeptides have since been discovered which exhibit biological activity in vitro. However, the characterization of target cells of these factors and the biological effects of the factors in vivo are essential for the identification of potential therapeutic applications in humans.

KGF is a known mitogen which has been previously identified as specific for epithelial cells, particularly keratinocytes. Rubin et al., *Proc. Natl. Acad. Sci. USA*, 86:802–806 (1989); Finch et al., *Science*, 245:752–755 (1989); Marchese et al., *J. Cell. Phys.* 144:326–332 (1990). Expression of messenger RNA for KGF has been detected in several stromal fibroblast cell lines derived from epithelial tissues of embryonic, neonatal and adult human sources, and in RNA extracted from normal adult kidneys and gastrointestinal tracts. Such RNA has not been detected in glial cells, lung cell 8, brain cell 8, or in a variety of epithelial cell lines that include squamous cell carcinomas, mammary epithelial cells, immortalized bronchial epithelial cells, immortalized keratinocytes, or primary keratinocyte cultures. Finch et al., Science, above. However, KGF is mitogenically active for the continuous mouse cell line, BALB/MK cells. Weissman and Aaronson, *Cell*, 32:599 (1983); also, see *PNAS* and *Science*, above. This observation supports evidence indicating a paracrine action of KGF in the skin, with production of KGF in the dermis (but not in the epidermis) and action on keratinocytes.

In addition, using the expression of keratins and filagrin genes it has been demonstrated that KGF influences the differentiation and maturation of keratinocytes. See *J. Cell Phys.*, above.

Much of the aforementioned work investigating the biological activity of KGF has been carried out with recombinant KGF, which has permitted more widespread study of this factor. Published PCT patent application WO 90/08771 describes the purification of KGF from the conditioned medium of a human embryonic fibroblast cell line, partial amino acid sequencing of the isolated polypeptide, cloning of the gene, and expression in bacterial cells (*E. coli*) to achieve recombinant, biologically active KGF.

While the role of KGF as a stimulatory agent for keratinocytes in vitro has been clearly identified, much remains to be known regarding KGF as a growth factor, including additional types of cells for which it may be targeted, and the effect of KGF on such cells in vivo. This information is vital for an understanding of the full potential of KGF as a therapeutic agent.

SUMMARY OF THE INVENTION

Briefly, the present invention concerns discoveries made with regard to the stimulatory effect of KGF on non-keratinocyte epithelial cells. More specifically, it has now been found that KGF used in vivo induces proliferation and differentiation in normal adnexal structures such as sebocytes and hair follicle cells, in liver cells such as hepatocytes, and in cells of the respiratory mucosal epithelium such as type II pneumocytes. There is also compelling evidence that KGF stimulates proliferation and growth of cells of the intestinal mucosa, e.g., mucin-producing goblet cells in the glandular stomach and small intestine, crypt cells in the colon, and other epithelial cells within the gut.

These discoveries, which form the basis of this invention, have significant implications in terms of enabling the application of KGF to tissues specifically characterized by damage to or deficiencies in these particular types of cells. The following is a description of diseases and medical conditions which can be treated with KGF in accordance with the invention.

Stimulation of proliferation and differentiation of adnexal structures such as hair follicles, sweat glands, and sebaceous glands is of critical importance in regenerating epidermis and dermis in patients with burns and other partial and full thickness injuries. At present, surface defects heal by scar formation and keratinocyte resurfacing; full regeneration of skin is not yet possible. Repopulation of hair follicles, sweat glands, and sebaceous glands does not occur presently in full thickness skin defects, including burns. The use of KGF can enable such repopulation. Standard in vivo models of adnexal structure proliferation and stimulation which permit the predictive testing of compounds having human therapeutic efficacy for burns and other partial and full-thickness injuries are well-known. Mustoe, et al. (1991), "Growth Factor-Induced Acceleration of Tissue Repair through Direct and Inductive Activities in a Rabbit Dermal Ulcer Model", *J. Clin. Invest.*, 87:694–703; Pierce, et al., "Platelet-derived Growth Factor (BB Homodimer), Transforming Growth Factor β-1, and Basic Fibroblast Growth Factor in Dermal Wound Healing", *American Journal of Pathology*, 140(6):1375 (1992)); and Davis, et al., "Second-Degree Burn Healing: The Effect of Occlusive Dressings and a Cream", *Journal of Surgical Research*, 48:245–248 (1990).

Epidermolysis bullosa is a defect in adherence of the epidermis to the underlying dermis, resulting in frequent open, painful blisters which can cause severe morbidity. Accelerated reepithelialization of these lesions, such as by treatment with KGF, would result in less risk of infection, diminished pain, and less wound care.

Chemotherapy-induced alopecia results when patients are treated with courses of chemotherapy for malignancy. At present no therapeutics are effective at preventing the hair follicle cells from death, which cause the transient loss of hair. KGF provides such a means. Standard in vivo models of chemotherapy-induced alopecia which permit the predictive testing of compounds having human therapeutic efficacy are well-known. Sawada, et al., "Cyclosporin A Stimulates Hair Growth in Nude Mice", *Laboratory Investigation*, 56(6):684 (1987); Holland, "Animal Models of Alopecia", *Clin. Dermatol*, 6:159:162 (1988); Hussein, "Protection from Chemotherapy-induced Alopecia in a Rat Model", *Science*, 249:1564–1566 (1990); and Hussein, et al., "Interleukin 1 Protects against 1-B-D-Arabinofuranosyulcytosine-induced Alopecia in the Newborn Rat Animal Model", *Cancer Research*, 51:3329–3330 (1991).

Male-pattern baldness is prevalent and essentially untreatable. The progressive loss of hair in men and women is a serious cosmetic problem. This condition could be treated using KGF either systemically, or topically if the drug could be applied and absorbed through the scalp, or by spray injection into the scalp using an air gun or similar technologies. A standard in vivo model of male-pattern baldness which permits the predictive testing of compounds having human therapeutic efficacy is well-known. Uno, "The Stumptailed Macaque as a Model for Baldness:effects of Minoxidil", *International Journal of Cosmetic Science*, 8:63–71 (1986).

Gastric ulcers, although treatable by H2 antagonists, cause significant morbidity and a recurrence rate, and heal by scar formation of the mucosal lining. The ability to regenerate glandular mucosa more rapidly, e.g., by treatment with KGF, would offer a significant therapeutic improvement in the treatment of gastric ulcers. Standard in vivo models of gastric ulcers which permit the predictive testing of compounds having human therapeutic efficacy are well-known. Tarnawski, et al., "Indomethacin Impairs Quality of Experimental Gastric Ulcer Healing: A Quantitative Histological and Ultrastructural Analysis", In:*Mechanisms of Injury, Protection and Repair of the Upper Gastrointestinal Tract*, (eds) Garner and O'Brien, Wiley & Sons (1991); and Brodie, "Experimental Peptic Ulcer", *Gastroenterology*, 55:25 (1968).

Duodenal ulcers, like gastric ulcers, are treatable, but the development of a therapeutic agent to more fully and more rapidly regenerate the mucosal lining of the duodenum would be an important advance. In addition, a therapeutic agent to regeneratively heal these ulcers and decrease their recurrence would be of benefit. KGF offers such potential. Standard in vivo models of duodenal ulcers which permit the predictive testing of compounds having human therapeutic efficacy are well-known. Berg, et al., "uodenal ulcers produced on a diet deficient in pantothenic acid", *Proc. Soc. Exp. Biol. Med.*, 7:374–376 (1949); Szabo and Pihan, "Development and Significance of Cysteamine and Propionitrile Models of Duodenal Ulcer", *Chronobiol. Int.*, 6:31–42 (1987); and Robert, et al., "Production of Secretatogues of Duodenal Ulcers in the Rat", *Gastroenterology*, 59:95–102 (1970).

Erosions of the stomach and esophagus, like erosive gastritis, esophagitis, or esophageal reflux, are treatable but the development of a therapeutic agent to more fully and rapidly regenerate the mucosal lining of the stomach and esophagus would be an important advance. In addition, a therapeutic agent to regeneratively heal these erosions and decrease their recurrence would be of benefit. KGF offers such potential. Standard in vivo models of erosion of the stomach and esophagus, like erosive gastritis, esophagitis, or esophageal reflux, which permit the predictive testing of compounds having human therapeutic efficacy are well-known. Geisinger, et al, "The histologic development of acid-induced esophagitis in the cat", *Mod-Pathol.*, 3(5):619–624 (1990); Carlborg, et al., "Tetracycline induced esophageal ulcers. A clinical and experimental study", *Laryngoscope*, 93(2):184–187 (1983); Carlborg, et al., "Esophageal lesions caused by orally administered drugs. An experimental study in the cat", Eur-Surg-Ethanol on esophageal motility in cats, *Alcohol-Clin-Exp-Res.*, 15(1):116–121 (1991), and Katz, et al., "Acid-induced esophophagitis in cats is prevented by sucralfate but not synthetic prostaglandin E.", *Dig-Dis-Sci.*, 33(2):217–224 (1988).

Inflammatory bowel diseases, such a Crohn's disease (affecting primarily the small intestine) and ulcerative colitis (affecting primarily the large bowel), are chronic diseases of unknown etiology which result in the destruction of the mucosal surface, inflammation, scar and adhesion formation during repair, and significant morbidity to the affected individuals. Therapy at present is designed to control the inflammation. A therapeutic such as KGF to stimulate resurfacing of the mucosal surface, resulting in faster healing, may be of benefit in controlling progression of disease. Standard in vivo models of inflammatory bowel disease which permit the predictive testing of compounds having human therapeutic efficacy are well-known. Morris, et al., "Hapten-induced Models of Chronic Inflammation and Ulceration in the Rat Colon", *Gastroenterology*, 96:795–803 (1989); Rachmilewitz, et al., "Inflammatory Mediators of Experimental Colitis in Rats", *Gastroenterology*, 97:326–327 (1989); Allgayer, et al., "Treatment with 16,16'-dimethyl-prostaglandin E2 before and after induction of colitis with trinitrobenzenesulfonic acid in Rats", *Gastroenterology*, 96:1290–1300 (1989); "Review:Experimental Colitis in Animal Models", *Scand. J. Gastroenterol*, 27:529–537 (1992).

Gut toxicity is a major limiting factor in radiation and chemotherapy treatment regimes. Pretreatment with KGF may have a cytoprotective effect on the small intestinal mucosa, allowing increased dosages of such therapies while reducing potential fatal side effects of gut toxicity. Standard in viva models of radiation-induced gut toxicity which permit the predictive testing of compounds having human therapeutic efficacy are well-known. Withers and Elkind, "Microcolony Survival Assay for Cells of Mouse Intestinal Mucosa Exposed to Radiation", *Int. J. Radiat.*, 17(3):261–267 (1970). Standard in viva models of chemotherapy-induced gut toxicity which are predictive of human therapeutic efficacy are well-known. Sonis, et al., "An Animal Model for Mucositis Induced by Cancer Chemotherapy, Oral Surg.", *Oral Med. Oral Pathol.*, 69:437–431 (1990); and Moore, "Clonogenic Response of Cells of Murine Intestinal Crypts to 12 Cytotoxic Drugs", *Cancer Chemotherapy Pharmacol.*, 15:11–15 (1985).

KGF treatment has a striking effect on the production of mucus throughout the gastrointenstinal tract. This property may be useful in protecting the gut mucosa from injuroious substances that are ingested, or in limiting the spread of injury in conditions such as inflammatory bowel diseases.

Hyaline membrane disease of premature infants results in the absence of surfactant production by type II pneumocytes within the lung, resulting in the collapse of the alveoli. Hyaline membrane disease may have both acute and chronic phases. The acute phase of hyaline membrane disease (Infant Respiratory Distress Syndrome—IRDS) is treated with mechanical ventilation and treatment with 80–100% concentrations of supplemental oxygen and by administration of an exogenous surfactant. Those patients undergoing a prolonged course of treatment may develop the chronic disease phase of hyaline membrane disease (bronchopulmonary dysplasia—BPD). While the surfactants have greatly reduced the mortality associated with IRDS, the morbidity associated with BPD remains high. Thus, there is a need to develop effective treatments to accelerate maturation of the lung and secretion of surfactant in neonates to reduce the incidence of BPD. Although corticosteroids can accelerate maturation and secretion in fetuses twenty-eight weeks old and beyond to a large extent, there is presently no treatment for younger fetuses, resulting in significant morbidity and mortality in this population. The history of BPD suggests that improvements in treatment of IRDS will be matched by mechanical ventilation of even smaller prematurely-born infants and a subsequent increase in the incidence of BPD in these smaller infants. A therapeutic agent such as KGF which would induce proliferation and differentiation of type II pneumocytes would be of considerable benefit in the treatment of this disease. Standard in vivo models of IRDS which permit the predictive testing of compounds having human therapeutic efficacy are well-known. Seider, et al., "Effects of antenatal thyrotropin-releasing hormone, antenatal corticosteroids, and postnatal ventilation on surfactant mobilization in premature rabbits", Am. J. Obstet. Gynec., 166:1551–1559 (1992); Ikegami, et al., "Corticosteroid and thyrotropin-releasing hormone effects on preterm sheep lung function", J. Appl. Physiol., 70:2268–2278 (1991). Standard in vivo models of BPD which permit the predictive testing of compounds having human therapeutic efficacy are well-known. Yuh-Chin, et al., "Natural surfactant and hyperoxide lung injury in primates I. Physiology and biochemistry", J. Appl. Physiol. 76:991–1001 (1994); and Galan, et al., "Surfactant replacement therapy in utero for prevention of hyaline membrane disease in the preterm baboon", Am. J. Obstet. Gynecol., 169:817–824 (1993).

Smoke inhalation is a significant cause of morbidity and mortality in the week following a burn injury, due to necrosis of the bronchiolar epithelium and the alveoli. A growth factor such as KGF which could stimulate proliferation and differentiation of these structures, and induce their repair and regeneration, would be of benefit in treating inhalation injuries. A standard in vivo model of smoke inhalation which permits the predictive testing of compounds having human therapeutic efficacy is well-known. Hubbard, et al., "Smoke inhalation injury in sheep", Am. J. Pathol., 133:660–663 (1988).

Emphysema results from the progressive loss of alveoli. A growth factor such as KGF which could stimulate regrowth or, is which cytoprotective for remaining alveoli would be of therapeutic benefit. At present, no effective treatment is available. A standard in vivo model of emphysema which permits the predictive testing of compounds having human therapeutic efficacy is well-known. "Induction of emphysema and bronchial mucus cell hyperplasia by intratracheal instillation of lipopolysaccharide in the hamster." J. Pathol., 167:349–56 (1992).

Hepatic cirrhosis, secondary to viral hepatitis and chronic alcohol ingestion, is a significant cause of morbidity and mortality. Cytoprotection, proliferation, and differentiation of hepatocytes such as by the use of KGF to increase liver function would be of benefit to slow or prevent the development of cirrhosis. A standard in viva model of hepatic cirrhosis which permits the predictive testing of compounds having human therapeutic efficacy is well-known. Tomaszewski, et al., "The production of hepatic cirrhosis in rats", J. Appl. Toxicol., 11:229–231 (1991).

Fulminant liver failure is a life-threatening condition which occurs with endstage cirrhosis. An agent such as KGF which could induce proliferation of remaining hepatocytes would be of direct benefit to this disease, which is presently treatable only with liver transplantation. Standard in vivo models of fulminant liver failure which permit the predictive testing of compounds having human therapeutic efficacy are well-known. Mitchell, et al., "Acetaminophen-induced hepatic necrosis I. Role of drug metabolism", J. Pharmcol. Exp. Ther., 187:185–194 (1973); and Thakore and Mehendale, "Role of hepatocellular regeneration in CC14 autoprotection", Toxicologic Pathol. 19:47–58 (1991).

Acute viral hepatitis is frequently subclinical and self-limiting. However, in a minority of patients, severe liver damage can result over several weeks. A cytoprotective agent such as KGF would be of use in preventing hepatocellular degeneration.

Toxic insults to the liver caused by acetaminophen, halothane, carbon tetrachloride, and other toxins could be ameliorated by a growth factor (KGF) which is cytoprotective for hepatocytes. Standard in vivo models of liver toxicity which permit the predictive testing of compounds having human therapeutic efficacy are well-known. Mitchell, et al. (1973), above and Thakore and Mehendale (1991), above).

Accordingly, the present invention encompasses the use of KGF therapeutically (or where appropriate, prophylactically) to treat the above mentioned conditions, as well as pharmaceutical preparations containing KGF in suitable, therapeutically effective amounts.

BRIEF DESCRIPTION OF THE DRAWINGS

FIG. 1 shows the nucleotide sequence of a synthetic oligonucleotide DNA used in the construction of a recombinant expression system for the KGF employed in the in vivo experiments described herein.

FIGS. 5A and 5B show a histologic analysis of Bromodeoxyuridine (BrdU)-treated hair follicles from KGF-treated and control wounds to show cellular proliferation in the modified rabbit model.

FIGS. 6A and 6B show oil red o staining of sebaceous glands from KGF-treated and control wounds of the same rabbit model.

FIGS. 15A and 15B show the increased weight of the gastrointestinal tract and liver in a dose-dependent fashion following treatment with KGF for four days.

DESCRIPTION OF SPECIFIC EMBODIMENTS

To identify specific types of epithelial cells in which KGF produces a significant biological effect indicative of potential therapeutic value, an extensive study was undertaken using live animals and KGF administration in vivo, with observation and analysis of the results. A recombinant KGF was used in each of the following Examples, which was prepared as follows:

The recombinant KGF gene was isolated from human foreskin fibroblast (AG1523) RNA by PCR and the resulting DNA ligated into a pCFM1156 expression vector between the NdeI and BamHI restriction sites. The plasmid pCFM1156 can be derived from the pCFM836 plasmid described in U.S. Pat. No. 4,710,473, incorporated herein by reference, by destroying the two endogenous NdeI restriction sites by end filling with T4 polymerase enzyme, followed by blunt end ligation and substituting the small DNA sequence between the unique ClaI and KpnI restriction sites with the following oligonucleotide duplex comprised of SEQ. ID NO.: 1 and SEQ. ID NO.: 2:

```
      ClaI                                                            KpnI
5'  CGATTTGATTCTAGAAGGAGGAATAACATATGGTTAACGCGTTGGAATTCGGTAC    3'
3'      TAAACTAAGATCTTCCTCCTTATTGTATACCAATTGCGCAACCTTAAGC      5'
```

The pCFM1156KGF plasmid was then cloned into FM5 host cells (ATCC #53911) using a standard electroporation (BioRad Gene Pulser™, BioRad Laboratories, Inc., 2000 Alfred Nobel Drive, Hercules, CA 94547) transformation procedure. To reduce an observed internal translational initiation, the DNA sequence in the KGF gene between KpnI and EcoRI was replaced with synthetic oligonucleotide DNA designed to reduce the use of an internal ribosomal binding site (FIG. 1). Following ligation and electroporation into FM5 cells (ATCC #53911), a clone containing pCFM1156KGF-dsd was selected. The DNA encoding the KGF gene was sequence confirmed. The cells were then cultured at 30° C. in 10-liter fermentors with a standard fed media that allows the cells to grow at an exponential rate under glucose limitation to prevent toxic byproduct accumulation. At mid-exponential cell density, the temperature was raised briefly to 42° C. to induce trancription of the KGF gene and then maintained at approximately 37° C. for the remainder of the KGF induction phase of the fermentation. Cell paste was collected and stored frozen. The biologically active KGF was purified from mechanically lysed cell paste by standard chromatography procedures that take advantage of the protein's very high isoelectric point (S-Sepharose Fast Flow by Pharmacia) and size (Superdex 75 by Pharmacia). The purified recombinant KGF protein was measured for endotoxin and biological activity in the mitogenic assay as described by Rubin et al. in PNAS, above.

EXAMPLE 1
KGF-STIMULATED PROLIFERATION AND DIFFERENTIATION OF ADNEXAL STRUCTURES IN AN IN VIVO WOUND HEALING MODEL

Figure 2:
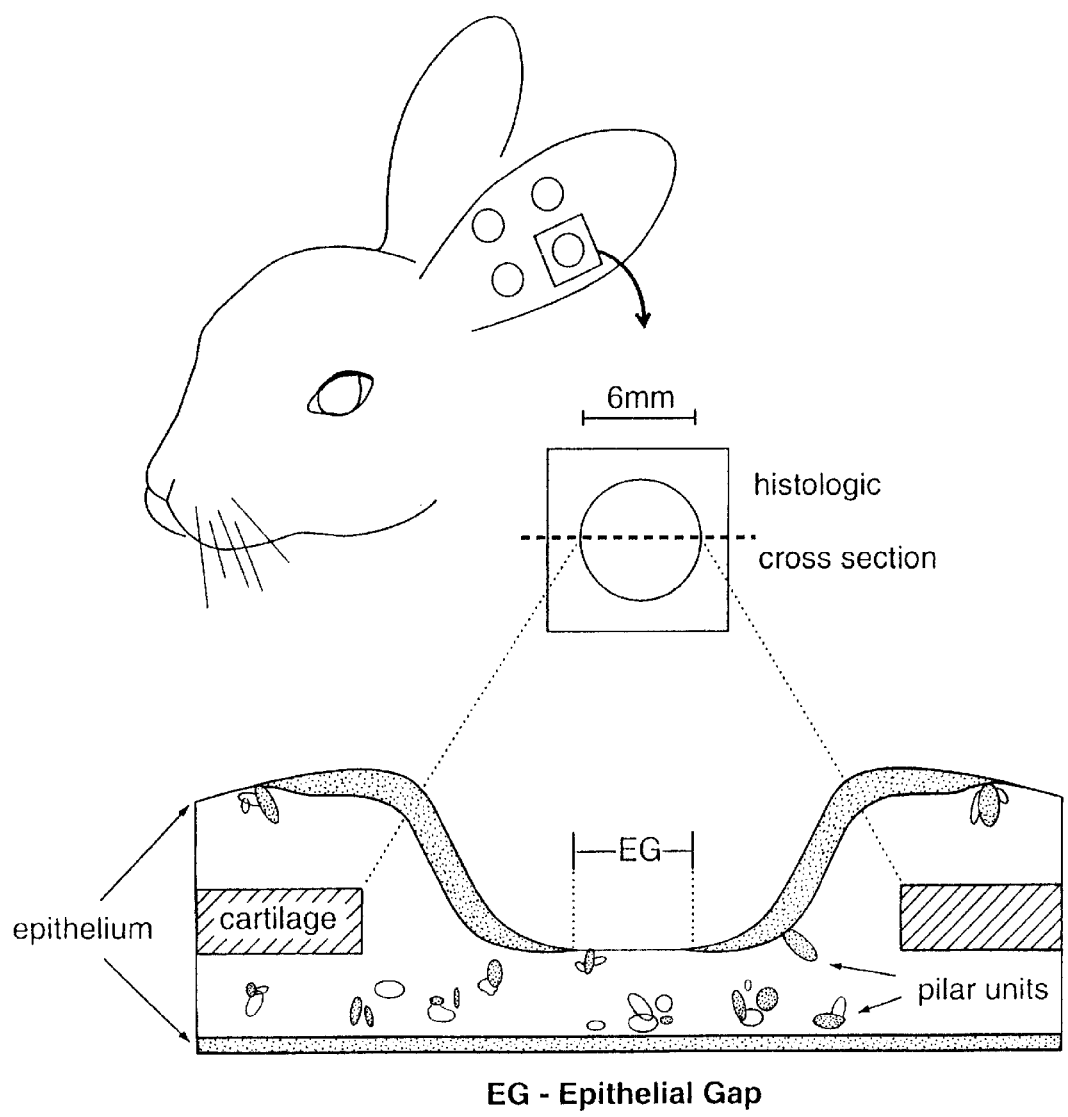
FIG. 2 depicts the rabbit ear partial thickness dermal wound model, as modified to produce a wound through the cartilage for better quantitation of new tissue growth.

In this Example, a modified rabbit ear partial thickness dermal wound model was used. The rabbit ear dermal ulcer model described by Mustoe et al., in *J. Clin. Invest.*, 87:694–703 (1991). was modified to produce a wound through the cartilage, to the dermis on the back side of the ear, using a 6 mm trephine. As a result, the wound heals by sprouting of epithelial elements beneath the cartilage, and contraction is not a variable during healing, permitting accurate quantitation of new tissues (See FIG. 2). Recombinant KGF, prepared as described above, was utilized as the therapeutic wound healing agent.

Materials and Methods

KGF or a phosphate buffered saline vehicle alone was applied once on the day of surgery and the wounds (0.25 $cm^2$) were covered with Tegaderm occlusive dressing (manufactured by 3M Company, St. Paul, Minn.). Prior to sacrifice, each animal received intravenous injections of BrdU (Aldrich Chemical Company, Milwaukee, Wis.), in an amount of 50 mg per kg of body weight. Administration of BrdU was employed to better quantify the degree of basal keratinocyte proliferation and the kinetics of basal cell migration toward the stratum spinosum and stratum corneum. After sacrifice, each wound was bisected, with one section being frozen in an optimum cooling temperature medium (OCT, Miles Inc., Elkhart, Ind.), and the second section being fixed in Omnifix (Al-Con, Genetics, Inc., Melville, Ny.) and processed according to routine histological methods. Masson Trichrome, oil red o, and immunohistochemical (IHC) stains were performed on 3 $\mu$m thick sections for each wound.

Measurement of Reepithelialization

Measurements of the total wound gap and epithelial gap were made for each wound using a calibrated stage micrometer. The percentage of reepithelialization for each wound was calculated by taking the difference of the total gap and the epithelial gap and dividing it by the total gap for each wound. Data from two sections per wound were averaged. Differences in the epithelial gap measurements and the percent of were analyzed by a one-tailed, unpaired Student's t-test.

The area of epithelium produced in treated and untreated wounds was calculated for each dose group. A one-way ANOVA and Dunnett's t-test was run for each dose against the control group.

Measurement of Proliferation and Differentiation of Epithelial Cells

Paraffin-embedded 3 μm sections of tissue were stained using anti-BrdU (Dako Corp. Carpinteria, Calif.), Avidin-Biotin Complex (Vector Laboratories, Inc., Burlingame, Calif.), and diaminobenzidine substrate (DAB, Sigma Chemical Co., St. Louis, Mo.). Sections were digested with 0.1% protease solution, followed by treatment with 2 N HCl. Endogenous peroxidase was quenched by exposure to 3% hydrogen peroxide solution. Slides were blocked with a 10% solution of normal horse serum in phosphate buffered saline (PBS), then incubated with anti-BrdU diluted 1:400 in 1% bovine serum albumin. Following washing, sections were incubated for twenty minutes with peroxidase-linked Avidin-Biotin Complex diluted 1:100 in 1% BSA. Slides were then exposed to DAB substrate (10 mg of DAB, 20 ml of PBS, 20 μl of 30% hydrogen peroxide) for ten minutes. Sections were counterstained with hematoxylin.

Histological Analysis of BrdU-treated Hair Follicles

Following BrdU incorporation and IHC staining, the total number of follicles per wound bed were counted and analyzed using the Kruskall-Wallis multiple comparison test. Further analysis included a Chi-square test on the percentage of wounds having follicles with ten or more proliferating cells in each treatment group. Additionally, the number of BrdU positive-staining cells was counted in all follicles having greater than five proliferating cells.

Oil Red O Staining of Sebaceous Glands

Oil red o, a stain specific for neutral lipids, was used for the identification of sebocytes and sebaceous glands, and was performed on frozen sections using the procedure described by F. L. Carson in *Histotechnology: A Self-Instructional Text;* ASCP Press, Chicago (1990). Briefly, 7 μm frozen sections were air dried and fixed in zinc-formalin for ten minutes. Slides were immersed on 0.3% w/v oil red o (Sigma Chemical Co., St. Louis, Mo.), then in 60% isopropanol for thirty minutes at room temperature, decolorized in 60% isopropanol, and counterstained with Learner's hematoxylin. The size of sebaceous glands and number of cells per gland were assessed.

Results and Discussion

Figures 3A, 3B:
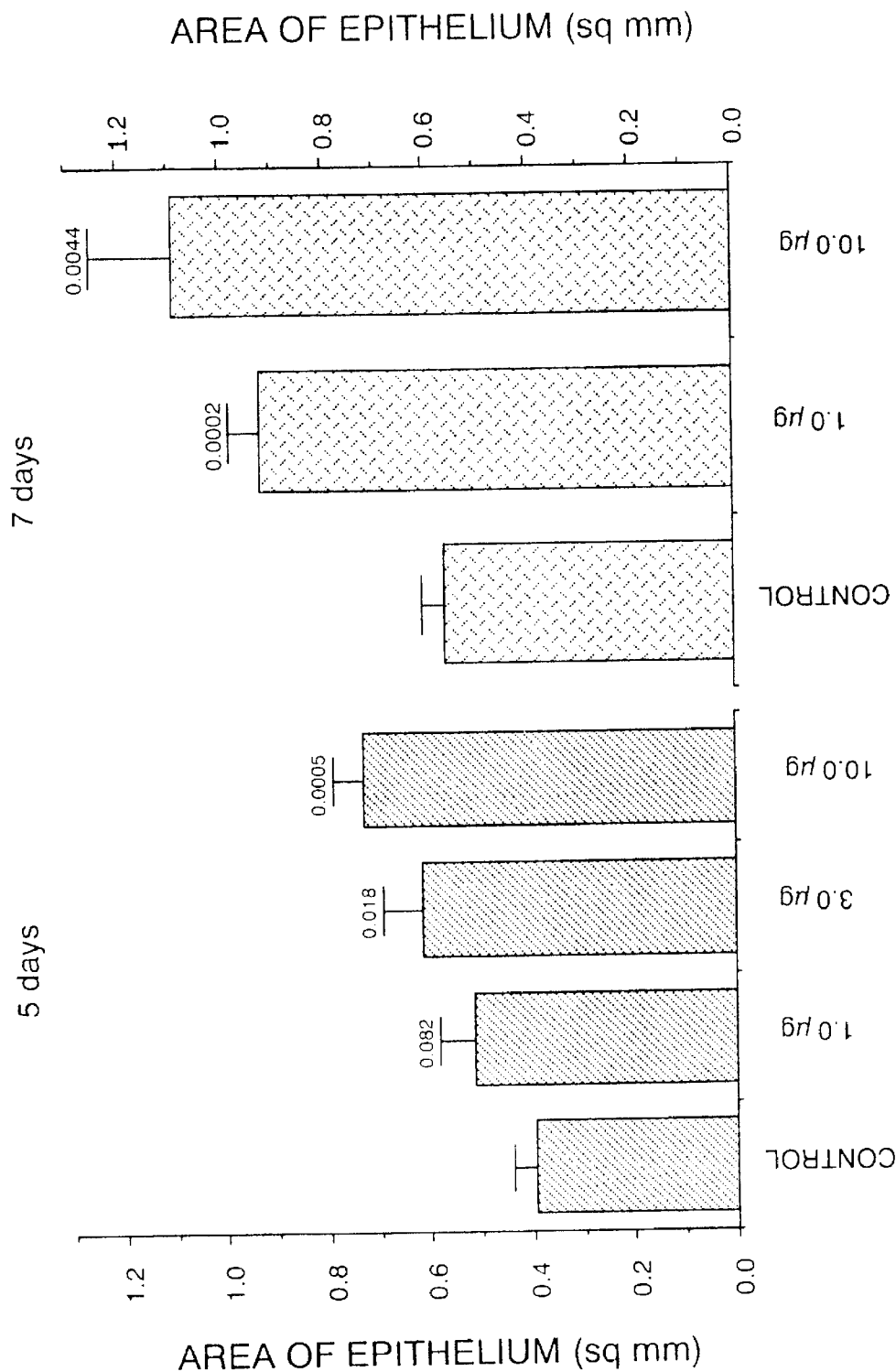
FIGS. 3A and 3B show depicts the reepithelialization of KGF-treated and control wounds from the modified rabbit ear partial thickness dermal wound model. The total area of regenerating epithelium after KGF treatment is shown on the left, and the percentage of reepithelialization of wounds is shown on the right.

Accelerated reepithelialization and increased thickness of epithelium was observed for wounds treated with 4–40 μg/cm$^2$ of KGF. Wounds on the fifth day post treatment showed significantly enhanced reepithelialization compared with the control (76.7% vs 52.5%, 1 μg of KGF). The thickness of new epithelium was increased in a dose-dependent manner by the fifth and seventh days of post treatment to nearly twice the area of the control wound epithelium at a dose of 10 μg of KGF per wound (FIGS. 3A and 3B). Histologic analysis suggested epithelial regeneration occurred largely by sprouting from adnexal elements within the dermis, i.e., sebaceous glands, sweat glands and hair follicles.

Figures 4A, 4B:
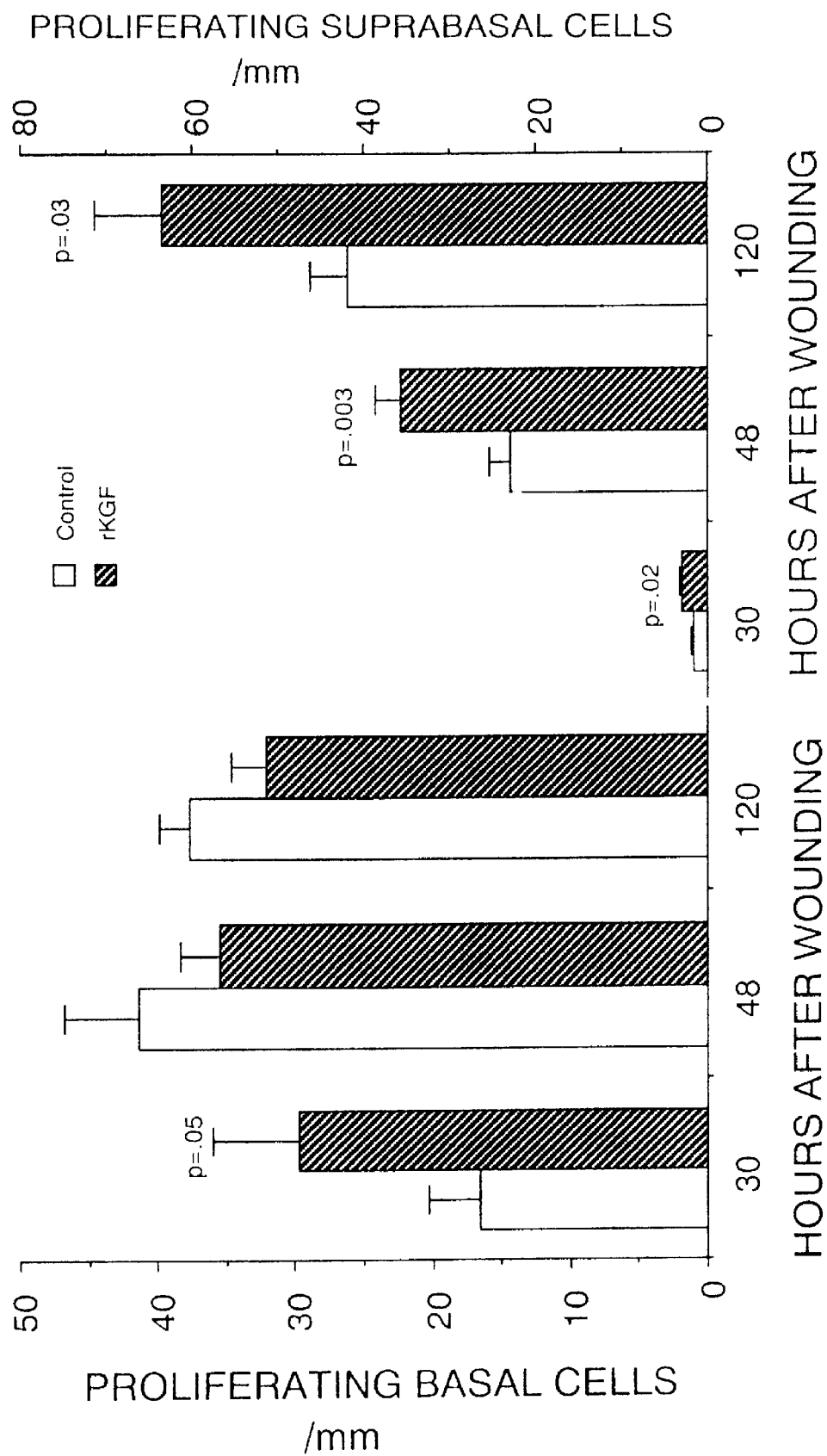
FIGS. 4A and 4B show the proliferation of basal and suprabasal keratinocytes at wound margins up to five days after KGF treatment, using the rabbit wound model.

Analysis of basal keratinocyte proliferation and basal cell migration revealed increased numbers of proliferating basal keratinocytes at the wound margins after the first day of KGF treatment (FIG. 4A). By the second day of KGF treatment, increased numbers of proliferating keratinocytes in the suprabasal layer of the epidermis suggested accelerated transit time of proliferating cells toward the stratum spinosum (FIG. 4B). By the fifth day of treatment, wounds showed less proliferation within the basal layer, indicating self-limited acceleration of epithelial repair and differentiation (FIG. 4A). Keratinocytes appeared to undergo normal maturation as they migrated upward to form the stratum corneum.

Unexpectedly, increased sebocyte proliferation and differentiation as well as increased hair follicle proliferation were also observed. Both hair follicles and sebaceous glands appeared larger and more numerous in KGF-treated wounds compared with control wounds (FIGS. 5A, 5B, 6A and 6B). Histologic sections which had been stained with oil red o to selectively identify sebaceous glands showed significantly increased numbers of such glands which were also markedly enlarged, indicating increased proliferation and differentiation of sebocytes into sebum-producing cells. Also, a dose dependent increase in the number of proliferating cells per hair follicle was observed in KGF-treated wounds.

Previously, epidermal growth factor (EGF) and basic fibroblast growth factor (FGF) have been examined in the rabbit ear model. *J. Clin. Invest.,* above, and Pierce et al., *Amer. J. Pathol.* 140:1375–1388 (1992). Although both of these growth factors are known to stimulate reepithelialization, neither EGF nor basic FGF influence proliferation or differentiation of adnexal structures such as sebaceous glands and hair follicles. The ability of KGF to stimulate proliferation and subsequent differentiation of multiple epithelial cell types within the skin, together with its original isolation from fibroblasts, suggests that KGF is a potent paracrine stimulator of the skin regenerative process.

EXAMPLE 2

KGF-STIMULATED PROLIFERATION AND DIFFERENTIATION OF IN VIVO TYPE II PNEUMOCYTES

This example was carried out to evaluate the effect of KGF administration on epithelial cells of the respiratory tract of healthy rats.

Materials and Methods

Male Lewis rats, weighing 200–250 grams each, received a single intratracheal injection of varying doses of KGF diluted in saline or phosphate buffered saline, using the protocol described by Ulich et al. in *Amer. J. Pathol.,* 138:1485–1496 (1991). KGF was injected at doses of 0.1, 1.0, 5.0 and 10.0 mg/kg. Control rats received an intratracheal injection of excipient. At time points of six hours and at one, two, three, four, five and six days after KGF injection the rats were sacrificed, the lungs were inflated with Bouin's fixative via an intratracheal catheter, saggital sections of the lung were paraffin-embedded, and histologic sections were stained with hematoxylin and eoxin.

Results and Discussion

Figure 7:
FIGS. 7 and 8 show micropapillary overgrowth of alveolar septal epithelial cells within the lungs of healthy rats which have been treated intratracheally with KGF.
Figure 8:
Figure 9:
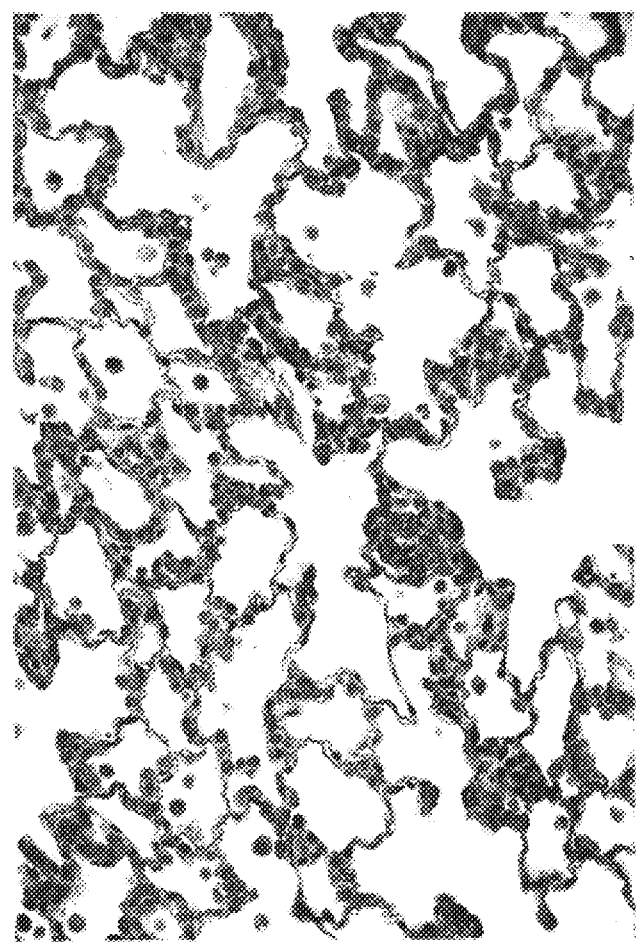
FIGS. 9 and 10 show cuboidal growth of epithelial cells in the alveoli of large segments of the lung after intratracheal administration of KGF to the same healthy rats.
Figure 10:
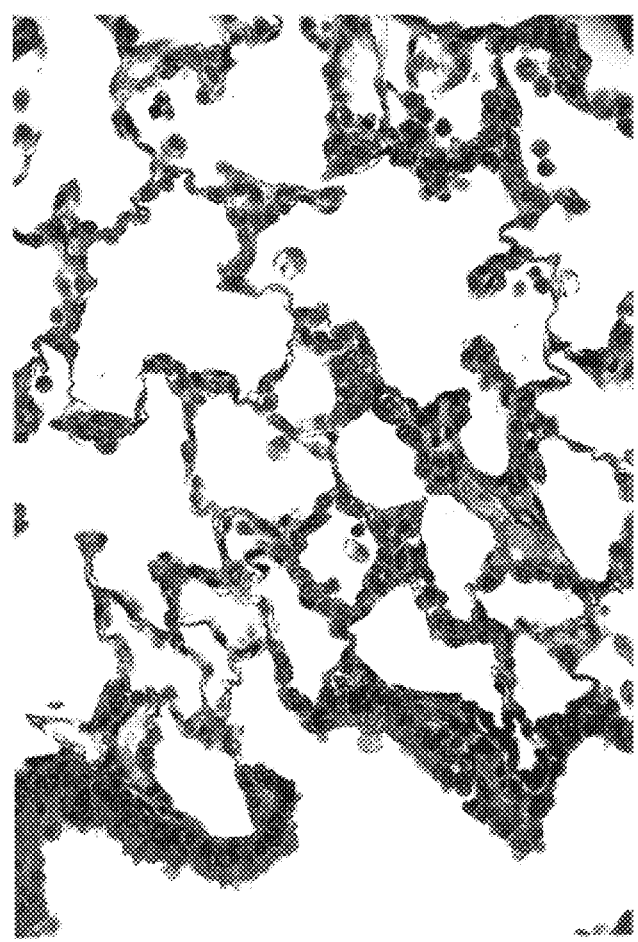

KGF at 0.1 mg/kg did not cause histologically discernible alveolar epithelial cell hyperplasia. KGF at 1.0 mg/kg caused a mild but definite increase in alveolar epithelial cells. Increasing alveolar epithelial cell hyperplasia was noted at 5.0 and 10.0 mg/kg, respectively. KGF did not cause a histologically discernible increase in alveolar epithelial cells at six hours or one day after intratracheal injection. At two days, a knobby micropapillary overgrowth of alveolar septal epithelial cells was noted within the lungs of KGF-treated rats (FIGS. 7, 8). At three days, a diffuse low-cuboidal to cuboidal growth of alveolar epithelial cells is noted lining entire alveoli in large segments of the lung (FIGS. 9, 10). Some areas of the lung, however, retained a normal histology. The histologic appearance of the hyperplastic alveolar epithelium in the rat on day three was essentially the same as the appearance of reactive type II pneumocyte hyperplasia in human lungs. Hyperplastic alveolar epithelium was recognizable in decreasing amounts in the lungs of KGF-treated rats on days four and five after intratracheal injection. On day six, the lungs of KGF-treated and control rats were indistinguishable.

Figure 11:
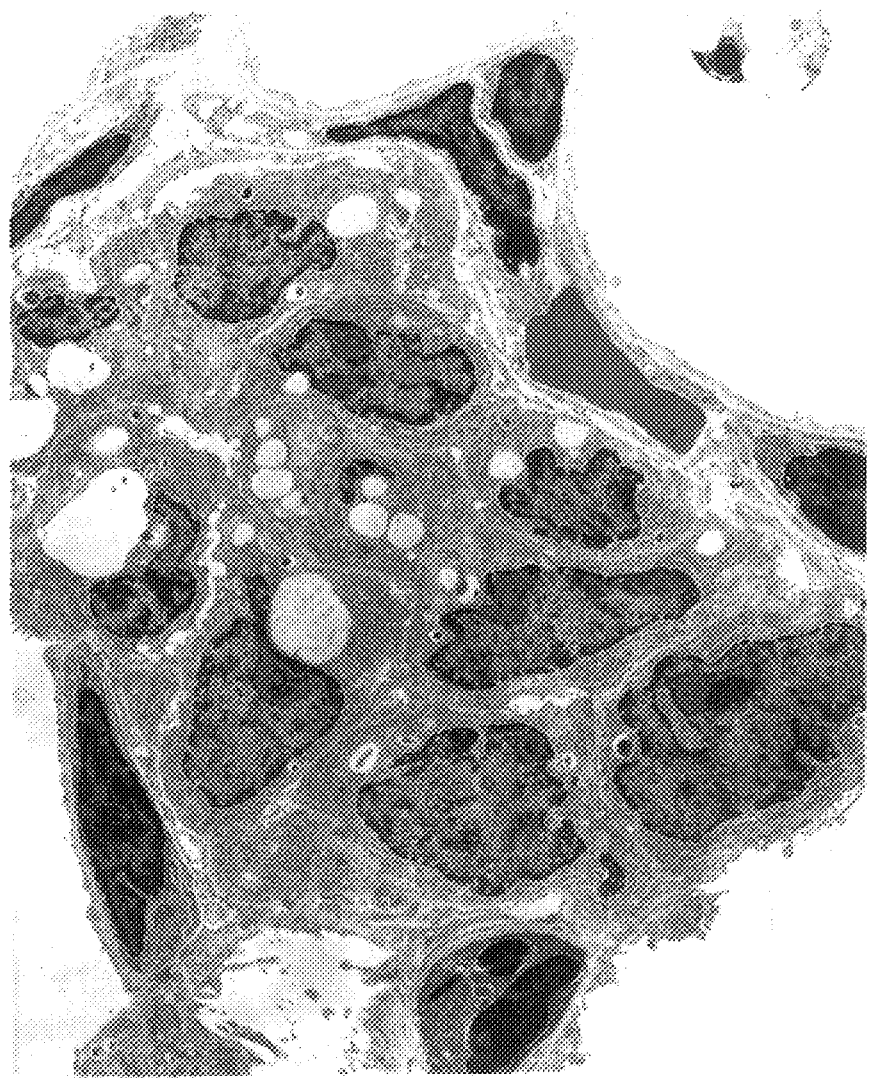
FIGS. 11 and 12 show that the hyperplastic alveolar epithelial cells lining the alveolar septae of such treated rats contain lamellar inclusions of varying size and shape.
Figure 12:
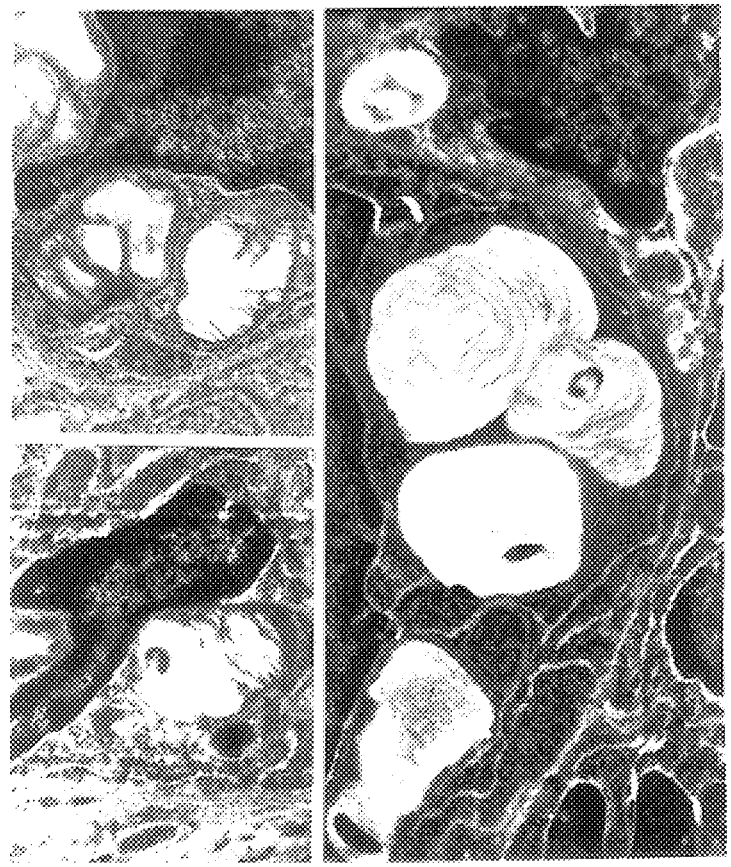
Figure 13A:
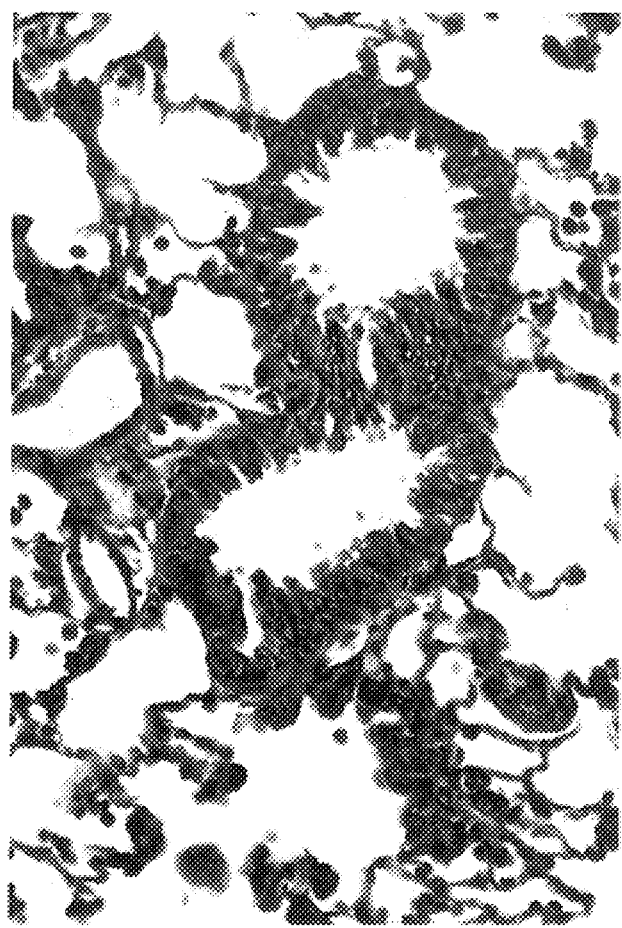
FIGS. 13A and 13B show hyperplastic effects of KGF treatment in the bronchial epithelium after intratracheal administration to healthy rats FIG. 13A, compared with a control FIG. 13B.
Figure 13B:
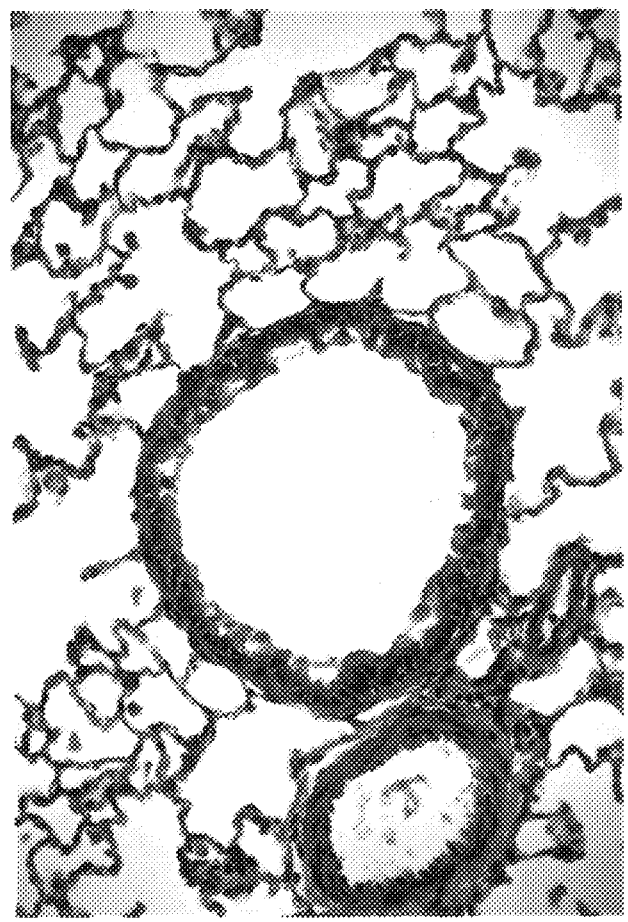

The lung of a KGF-treated rat was ultrastructurally examined three days after intratracheal injection. The hyperplastic alveolar epithelial cells lining the alveolar septae almost invariably contained one or more lamellar inclusions of varying size and shape (FIGS. 11, 12). The bronchial epithelium of KGF-treated rats was hyperplastic on day three, but the hyperplasia was not as immediately striking as the alveolar cell hyperplasia. Hyperplasia was appreciated as pseudostratification of the epithelial lining of smaller distal bronchi that are normally lined by a single layer of epithelium, by tufting or micropapillary growth of bronchial epithelium, and by an increase in mitotic figures within the bronchial epithelium (FIGS. 13A, 13B).

KGF administered intratracheally causes a striking hyperplasia of alveolar epithelial cells. The presence of lamellar cytoplasmic inclusions within the cells at the ultrastructural level is consistent with the proposal that the hyperplastic cells are type II pneumocytes. The lamellar inclusions did not appear as numerous or as osmiphilic as those illustrated in some cases of experimental type II pneumocyte hyperplasia in the rat, but are very similar to the lamellar inclusions illustrated in normal rat lung. In addition to causing alveolar cell hyperplasia, KGF causes bronchial epithelial cell hyperplasia. It is possible that the hyperplastic alveolar epithelium represents a downgrowth of bronchial epithelium from terminal bronchioles into the alveolar parenchyma. However, it appears more likely that KGF acts directly on type II pneumocytes because of the multifocal micropapillary budding growth pattern of pneumocytes on alveolar septae two days after injection of KGF, a growth pattern that precedes the confluent lining of the alveoli by cuboidal cells on the third day. In addition, type II pneumocytes are thought to be the mitotically responsive alveolar epithelial cell population and would be expected to be the alveolar cell type to respond to a potential endogenous mediator of alveolar cell growth such as KGF. Finally, the identification of lamellar inclusions within the hyperplastic cells suggests not only their differentiation into type II pneumocytes but also their origin from type II pneumocytes.

The stimulatory effect of KGF on type II pneumocytes is consistent with the observation that the amount of KGF receptor messenger RNA in the lungs per equivalent sample of total RNA is two to three times the level found for various other organs from young adult rats. In this experiment, KGF receptor messenger RNA levels were detected using a modified Ambion RNAse Protection Assay (RPA II, No. 1410).

The "antisense" RNA probe used in this assay had the following sequence (SEQ. ID NO.: 3):

```
5' GAAUACGAAUUCCUUGCUGUUUGGGCAGGACAGUGA—
   GCCAGGCAGACUGGUUGGCCUGCCCUAUAUAAUUGG—
   AGACCUUACAUAUAUAUUCCCCAGCAUCCAUCUCCG—
   UCACAUUGAACAGAGCCAGCACUUCUGCAUUGGAGC—
   UAUUUAUCCCCGAGUGGAUC 3'
```

The antisense probe was prepared using a Promega Riboprobe Gemini II kit (#P2020) from a linearized template DNA encoding the corresponding DNA sequence described above. The RNA probe was purified from a urea-polyacrylamide gel by cutting out the correct size band and eluting the RNA probe in Ambion Solution F.

The "sense" RNA standard coding for the complement RNA sequence to the "antisense" probe is as follows (SEQ. ID NO.: 4):

```
5' GGGAGACAAGCUUGCAUGCCUGCAGGUCGACUCUAG—
   AGGAUCCACUCGGGGAUAAAUAGCUCCAAUGCAGAA—
   GUGCUGGCUCUGUUCAAUGUGACGGAGAUGGAUGCU—
   GGGGAAUAUAUAUGUAAGGUCUCCAAUUAUAUAGGG—
   CAGGCCAACCAGUCUGCCUGGCUCACUGUCCUGCCCA—
   AACAGCAAGG 3'
```

The sense standard was prepared cold (without radioactive label) using the Promega Riboprobe Gemini II kit (#P2020) and purified over a G50 Sephadex Quick spin column.

Following the standard Ambion (RPA II #1410) protocol, 50 ug of total RNA were incubated with $10^5$ cpm of probe, first at 95° C. for four minutes, then twelve to eighteen hours at 45° C. RNAse (1:500 Ambion Solution R) was incubated with the hybridization solution at 37° C. for forty minutes, followed by addition of the inactivating/precipitation reagent (Solution Dx).

Figure 14:
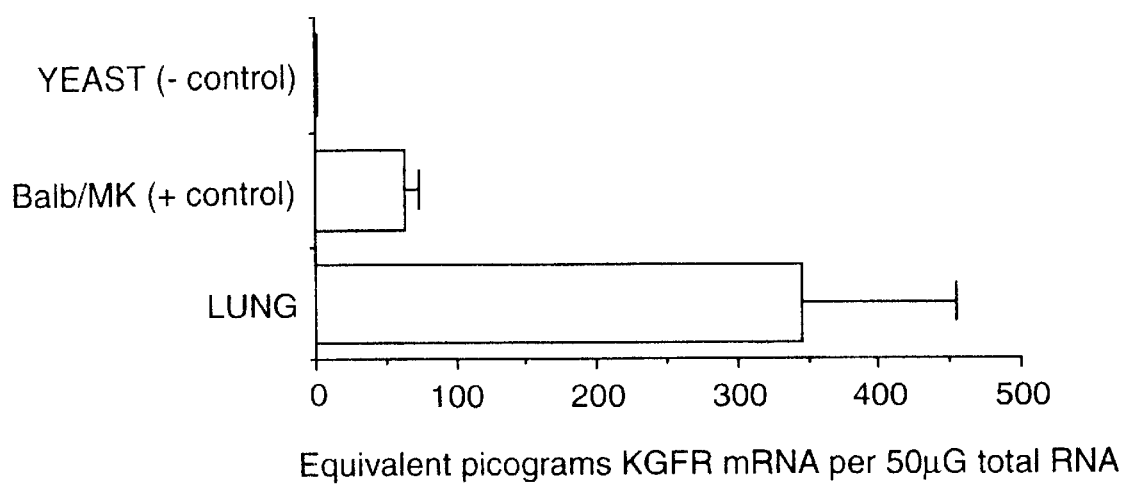
FIG. 14 depicts the results of an RNase protection assay for the KGF receptor (KGFR) in the adult rat lung.

The RNAse protected fragments were then separated by size using urea-polyacrylamide gel electrophoresis and the whole gel was exposed to a phosphorimager screen. The bands were then quantified on a Molecular Dynamics Phosphorimager. The results are shown in FIG. 14.

The identification of KGF as a growth factor for type II pneumocytes raises the possibility that KGF will show therapeutic potential similar to glucocorticoids as a stimulant of fetal lung maturation. KGF might also be clinically useful in stimulating bronchoalveolar repair after lung injury in the adult. The proliferative effect of KGF on type II pneumocytes suggests that KGF may play an important role in regulating the synthesis and secretion of surfactant.

EXAMPLE 3
KGF-STIMULATED PROLIFERATION AND DIFFERENTIATION OF HEPATOCYTES

The effects of systemically administered KGF the epithelial tissues of the liver in adult rats were evaluated.

Materials and Methods

Male rats received water and food ad libitum. All animals received either KGF or PBS by intraperitoneal injection daily, for one, four, or seven days. In all experiments, at least five animals were analyzed per group.

All rats were euthanized by $CO_2$ asphyxiation and blood was obtained for serum chemistry by cardiac puncture immediately postmortem and stored frozen until assayed. Serum was analyzed for standard serum chemistries and electrolytes. The liver was weighed in a blinded fashion and weights were expressed as grams per 100 grams body weight (percent body weight). Tissue samples were placed in 10% buffered formalin for routine histological processing.

Sections from the liver were stained with hematoxylin and eosin (H and E). One hour prior to sacrifice, rats received 50 mg/kg of BrdU via intraperitoneal injection. Anti-BrdU immunohistochemistry was performed to visualize BrdU incorporation into DNA of replicating cells.

The labeling index (LI) of the liver was determined using a calibrated eye objective grid. Ten fields per animal were counted and averaged. Total nuclei and labeled nuclei per unit area were counted. To standardize the fields counted as representing similar areas of hepatic parenchyma, all fields counted were adjacent to a portal triad.

All data was analyzed using an unpaired two-tailed Student's t-test or one-way ANOVA for multiple group comparison.

Results and Discussion

Figures 16A, 16B:
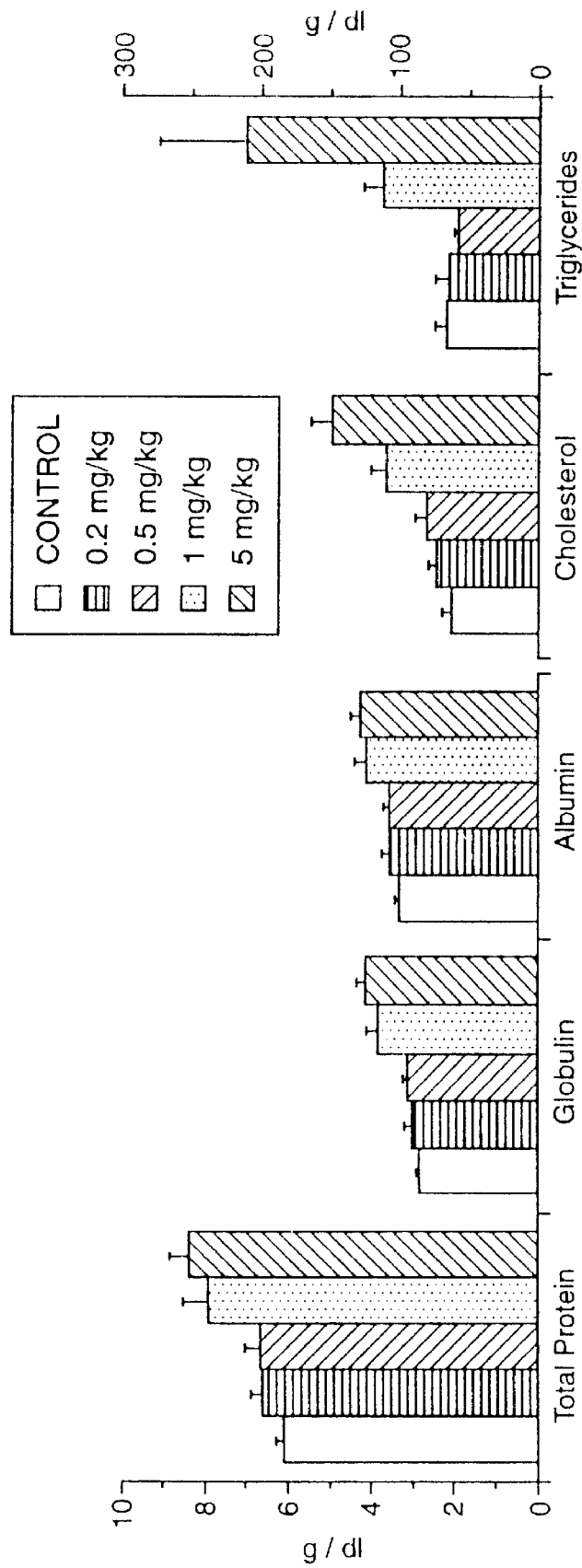
FIGS. 16A and 16B show the increase in protein synthesis by the liver in rats treated with KGF for four days in dose-dependent manner.

A dose response study was performed to identify an effective dose of KGF. KGF was injected daily for four days, and organs were harvested. Liver, expressed as percent body weight, was significantly different from controls only at the highest dose of 5 mg/kg per day when compared by ANOVA (FIG. 15A and 15B). Of note, serum proteins, cholesterol and triglycerides, compounds synthesized by the liver were significantly higher compared with controls at both 1 and 5 mg/kg of KGF (FIG. 16A and 16B).

Animals were analyzed after one, four, or seven days daily treatment with KGF at 5 mg/kg. Upon gross necropsy exam, the liver was notably enlarged at the seven-day time point. Liver weight was significantly increased at all study time points in KGF-treated rats (day seven, KGF 4.08±0.08% vs. control 3.49±0.06%, p=0.0003).

Figures 17A, 17B:
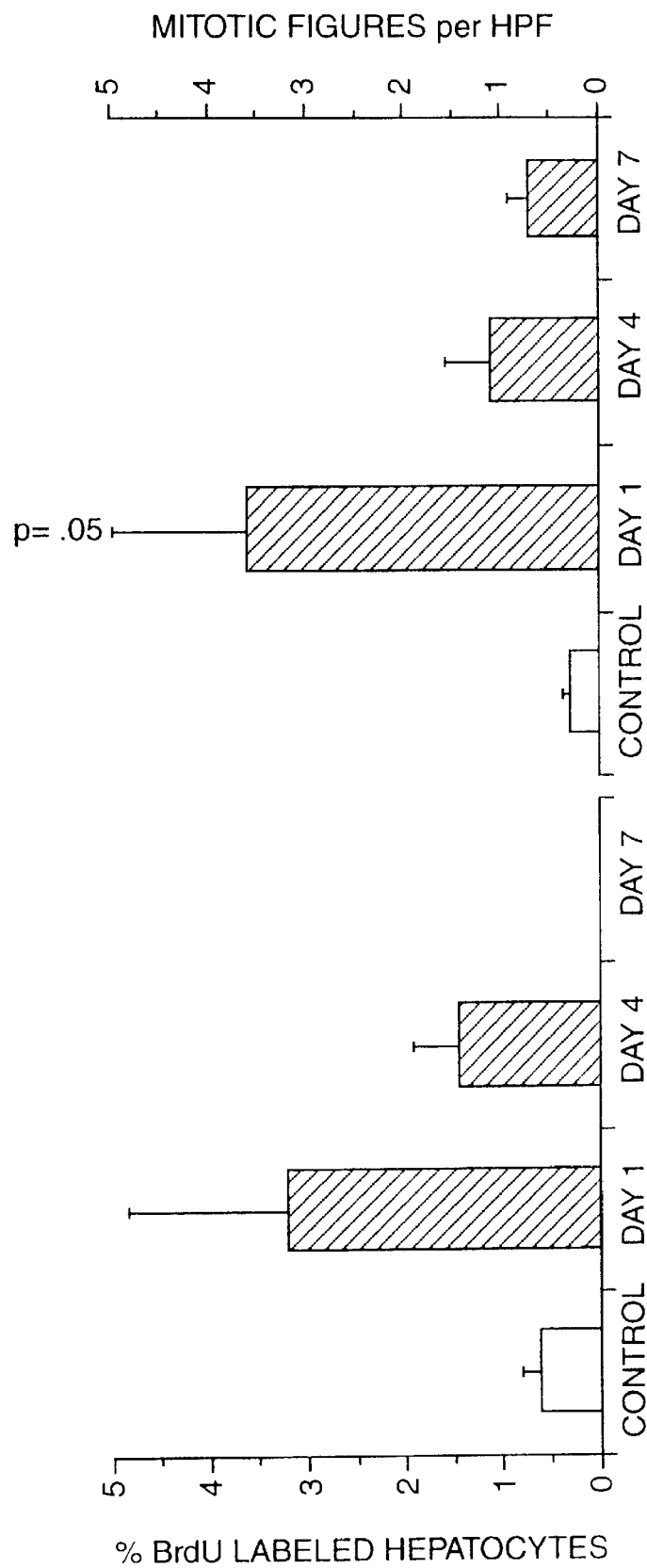
FIGS. 17A and 17B show the increased proliferation of hepatocytes within the liver of animals treated for one to seven days with KGF, assessed using BrdU labeling FIG. 17A or mitotic counts FIG. 17B.

Quantitation of BrdU-positive nuclei demonstrated three- to four-fold increases in KGF-treated rats compared with controls at one day (FIG. 17A and 17B). Mitotic Index expressed as mitotic figures per high powered field was significantly elevated over controls at one-day treatment, consistent with the BrdU counts.

These results demonstrate potent mitogenic and differentiation effects of KGF on the liver. The rapid increase in liver weight after one day of KGF treatment coupled with an elevated mitotic index and BrdU-positive fraction demonstrates the rapid and potent effects of KGF on this predominantly epithelial tissue. Though the mitotic effects of KGF drop off rapidly, the liver weight expressed as percent body weight continued to increase throughout the studies. The increased weight was primarily due to an increase in cells that was histologically observable as early as one day and persisted through four and seven days of treatment. Since liver mass can increase by greater than two-fold in less than two weeks during liver regeneration, it was not surprising to find marked differences beginning after one day treatment.

Elevated levels of albumin are not associated with any known disease state other than dehydration. KGF was likely inducing greater serum levels of albumin (and other proteins) due to the increased number of hepatocytes which were present. Increased protein synthesis induced by KGF would be of tremendous lifesaving benefit to individuals with end stage liver disease or cirrhosis.

EXAMPLE 4
KGF-STIMULATED PROLIFERATION AND RECOVERY OF LIVER CELLS IN VIVO FOLLOWING PARTIAL HEPATECTOMY

In this experiment, male Sprague-Dawley rats, each weighing from 300 to 340 grams, were used as the test subjects.

Materials and Methods

Each of the rats was subjected to two-thirds partial hepatectomy using the procedure of Higgins and Anderson, *Archives of Pathology*, 12:186 (1931). Commencing eight hours following surgery, and continuing once a day thereafter, the rats were injected subcutaneously with either PBS (control group) or KGF at a dose of 1 mg/kg. The control and KGF-treated rats were weighed and sacrificed four, seven, ten, or fourteen days after surgery. Liver remnants were then removed and weighed.

Results and Discussion

Figure 18:
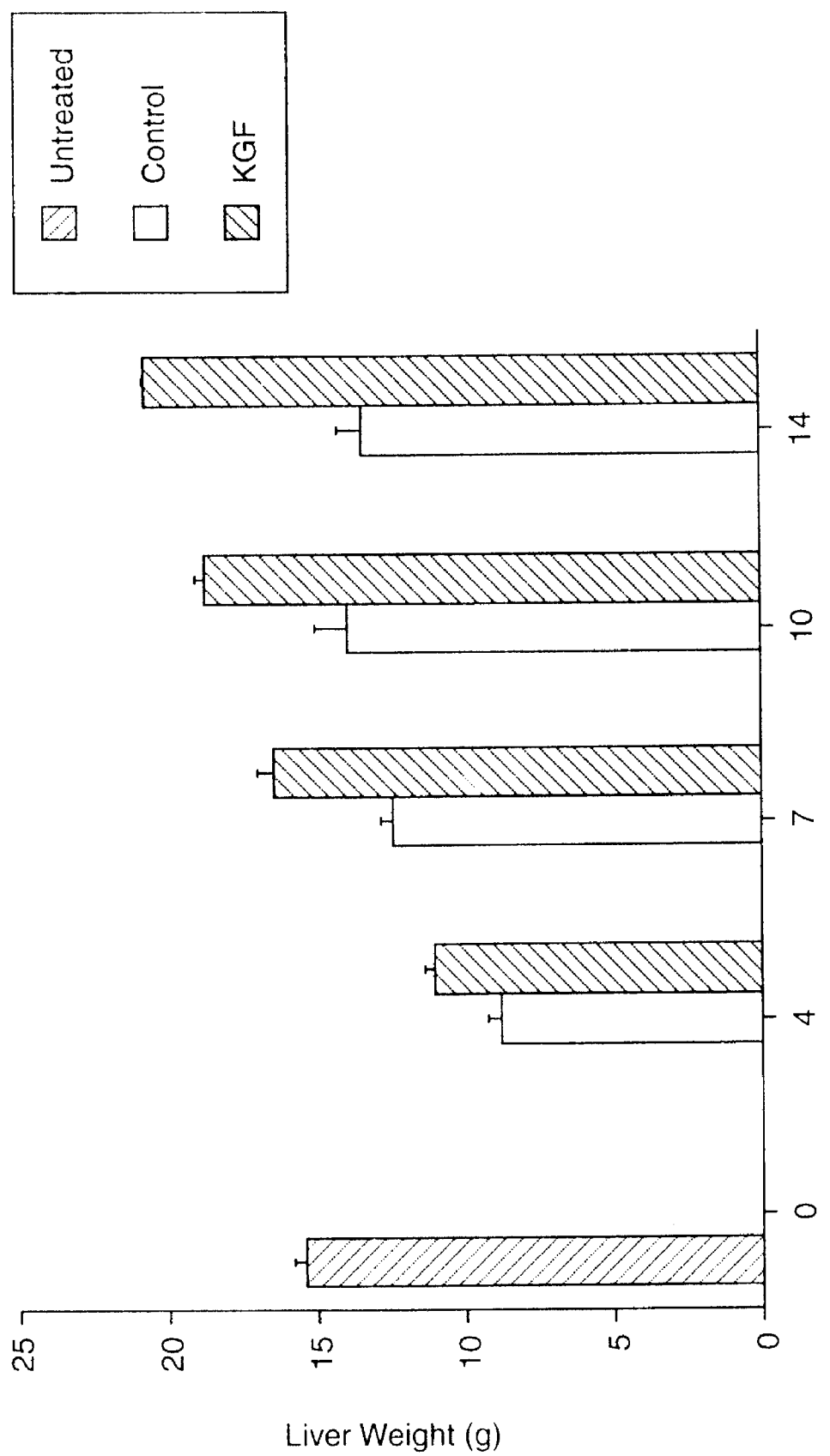
FIGS. 18 and 19 depict the recovery in liver mass, following treatment with KGF, of partially hepatectomized rats.
Figure 19:
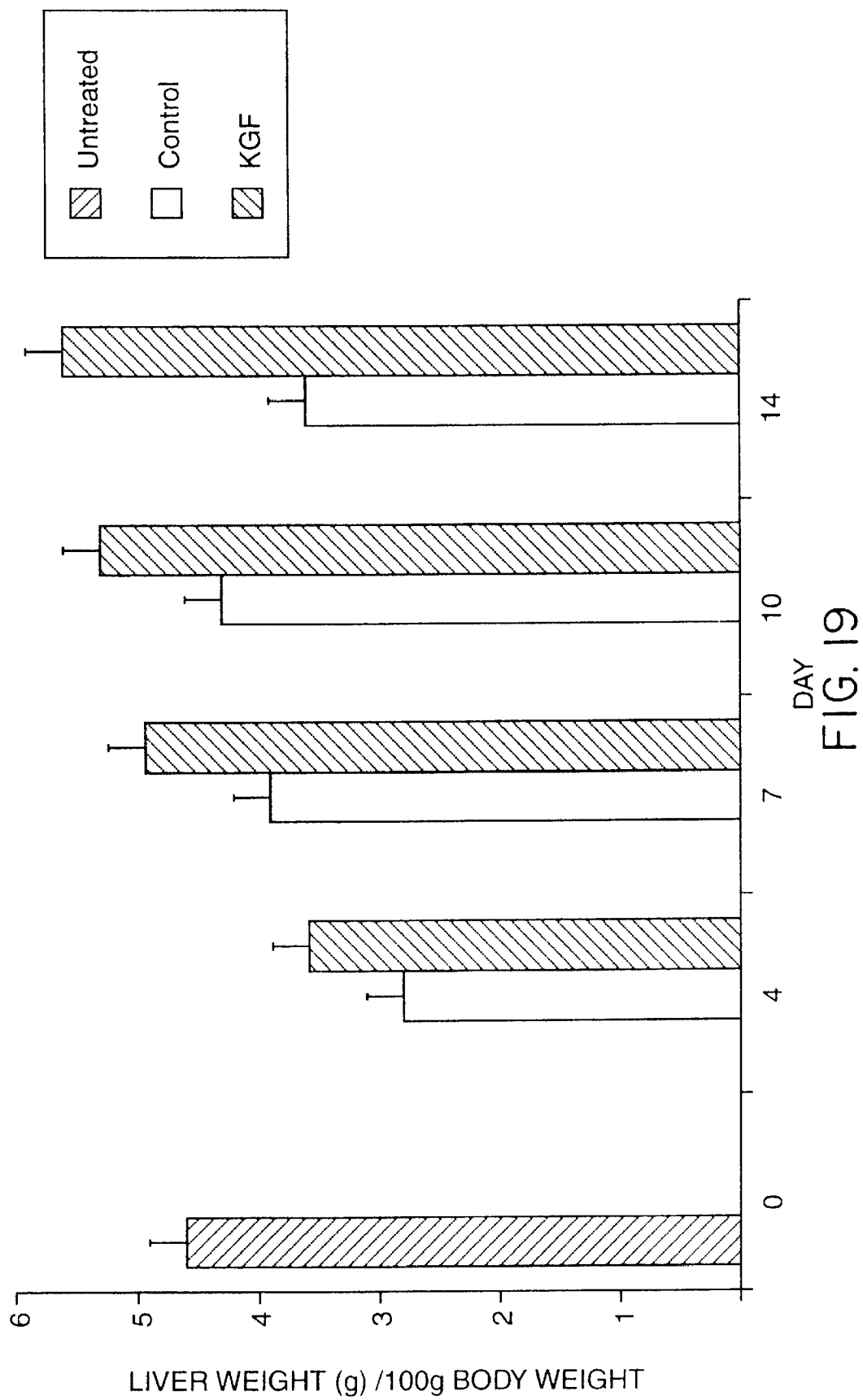

It was found that treatment of partially hepatectomized rats with KGF resulted in significant acceleration in the recovery of liver mass, both on an absolute and relative basis, as shown in FIGS. 18 and 19, respectively. In the KGF-treated group liver mass returned to pre-surgical values within seven days. By contrast, for the control (non-KGF treated) group neither absolute nor relative liver mass was completely restored even after fourteen days.

EXAMPLE 5
AMELIORATIVE EFFECT OF KGF ON CHEMICAL INDUCED LIVER TOXICITY

Male Sprague-Dawley rats, weighing 300 to 340 grams each, were tested to evaluate the therapeutic effect of KGF on the liver after introduction of a chemical toxin.

Administration

Groups of twelve male Sprague-Dawley rats were given either 1 ml/kg or 2 ml/kg of carbon tetrachloride ($CCl_4$) in a corn oil vehicle on day zero. Each dosage group was subdivided into two subgroups of six rats each. Beginning at three hours after $CCl_4$ administration, and continuing daily thereafter, each subgroup was injected subcutaneously with either PBS or 1 mg/kg/day of KGF. At twenty-two, seventy-two and one hundred and forty-four hours after $CCl_4$ administration, a blood sample was taken from each rat and the serum glutamate-oxaloacetate transaminase (SGOT) level was determined.

Results and Discussion

Figure 20:
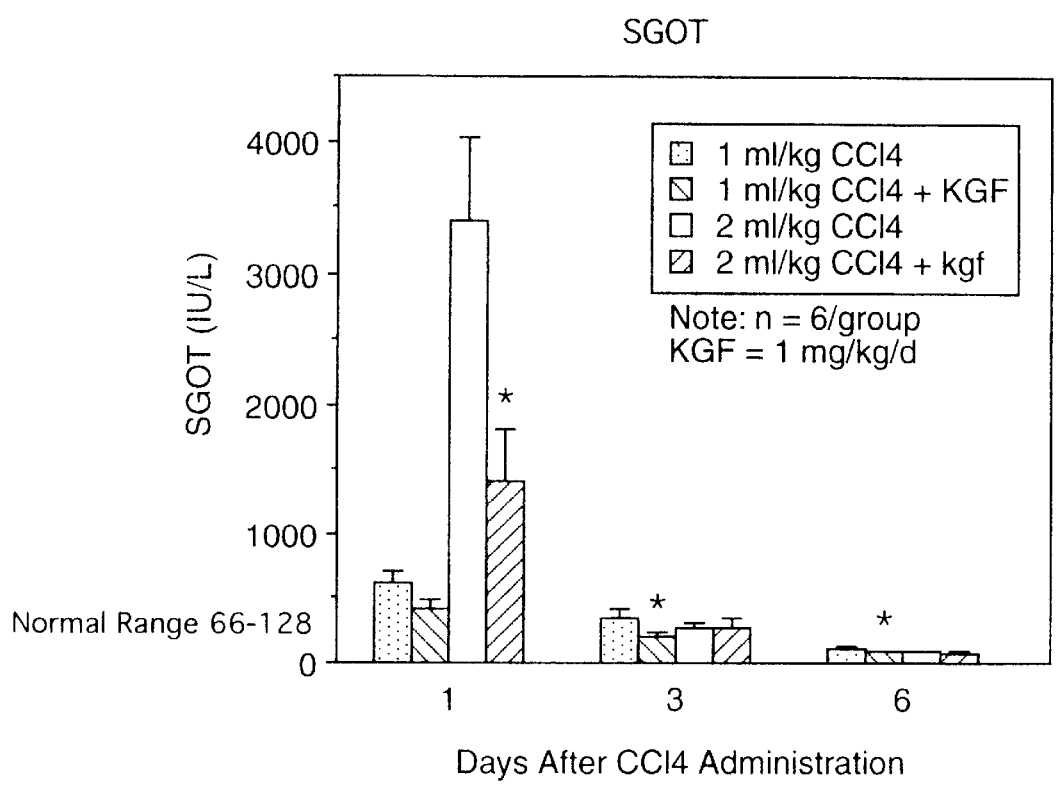
FIG. 20 depicts the decrease in blood serum levels of serum glutamate-oxaloacetate transaminase (SGOT) in carbon tetrachloride poisoned rats, following treatment with KGF.

As shown in FIG. 20, subcutaneous injection of KGF after oral administration of $CCl_4$ significantly decreased blood serum levels of an enzyme (SGOT) which is a known indicator of liver damage. The effect is especially pronounced at 2 ml/kg, on the first day after administration.

EXAMPLE 6
KGF-STIMULATED PROLIFERATION AND DIFFERENTIATION OF EPITHELIAL CELLS OF THE INTESTINAL MUCOSA

This Example evaluates the biological effects of KGF on epithelial cells of the intestinal mucosa of healthy rats.

Materials and Methods

Male rats received water and food ad libitum. All animals received either KGF or PBS by intraperitoneal injection daily for one, four or seven days. In all experiments, at least five animals were analyzed per group.

All rats were euthanized by $CO_2$ asphyxiation. Major organs were weighed in a blinded fashion and weights were expressed as grams per 100 grams body weight (percent body weight). The gut was divided into the non-glandular foregut, glandular stomach, small intestine, and large intestine. Tissue samples were placed in 10% buffered formalin for routine histological processing.

Sections from all organs harvested were stained with hematoxylin and eosin (H and E). One hour prior to sacrifice, rats received 50 mg/kg BrdU via intraperitoneal injection. Anti-BrdU immunohistochemistry was performed using standard methods to visualize BrdU incorporation into DNA of replicating cells. Selected tissues were stained with periodic-acid-schiff (PAS), Alcian blue at pH 2.5, and Masson-Trichrome.

A calibrated ocular was used to measure the heights of the gastric mucosa and the depth of PAS staining with the gastric mucosa. Similarly, the length of villi and depth of intestinal crypts in the duodenum and the depth of the colonic crypts in the colon were measured. To quantify the changes in goblet cell production, the number of PAS positive goblet cells was counted along 100 μm lengths beginning at the base of the duodenal villi. In all areas of the gut, measurements were made only on glands or villi that were perpendicular to the underlying muscularis. Results are recorded in microns or in the case of small intestinal goblet cells the average number per unit area. In addition, the number of colonic crypts and the number of hyperplastic (bifurcated or trifurcated) crypts occupying a defined length of colon were determined. Five to ten replicate measurements were made per animal and the averaged. All data was analyzed using an unpaired two-tailed Student's t-test or one-way ANOVA for multiple group comparisons (Statview II, Abacus Concepts, Berkeley, Calif.).

Results and Discussion

A dose response study was performed initially to identify an effective dose of KGF. KGF was injected daily for four days, and organs were harvested. A pronounced dose response was observed in the glandular stomach, small intestine, and colon (FIG. 15A and 15B).

Animals were analyzed after one, four and seven days daily treatment with KGF at 5 mg/kg. Upon gross necropsy exam, the foregut was grossly thickened with folding of the mucosa at four- and seven-day treatment. The foregut, glandular stomach, duodenum and colon showed significant weight increases at four and seven days, but not at one-day treatment. At seven days, the glandular stomach was $0.65 \pm 0.01$ g in KGF-treated animals, and $0.48 \pm 0.02$ g in controls (p=0.001).

Figures 21A, 21B:
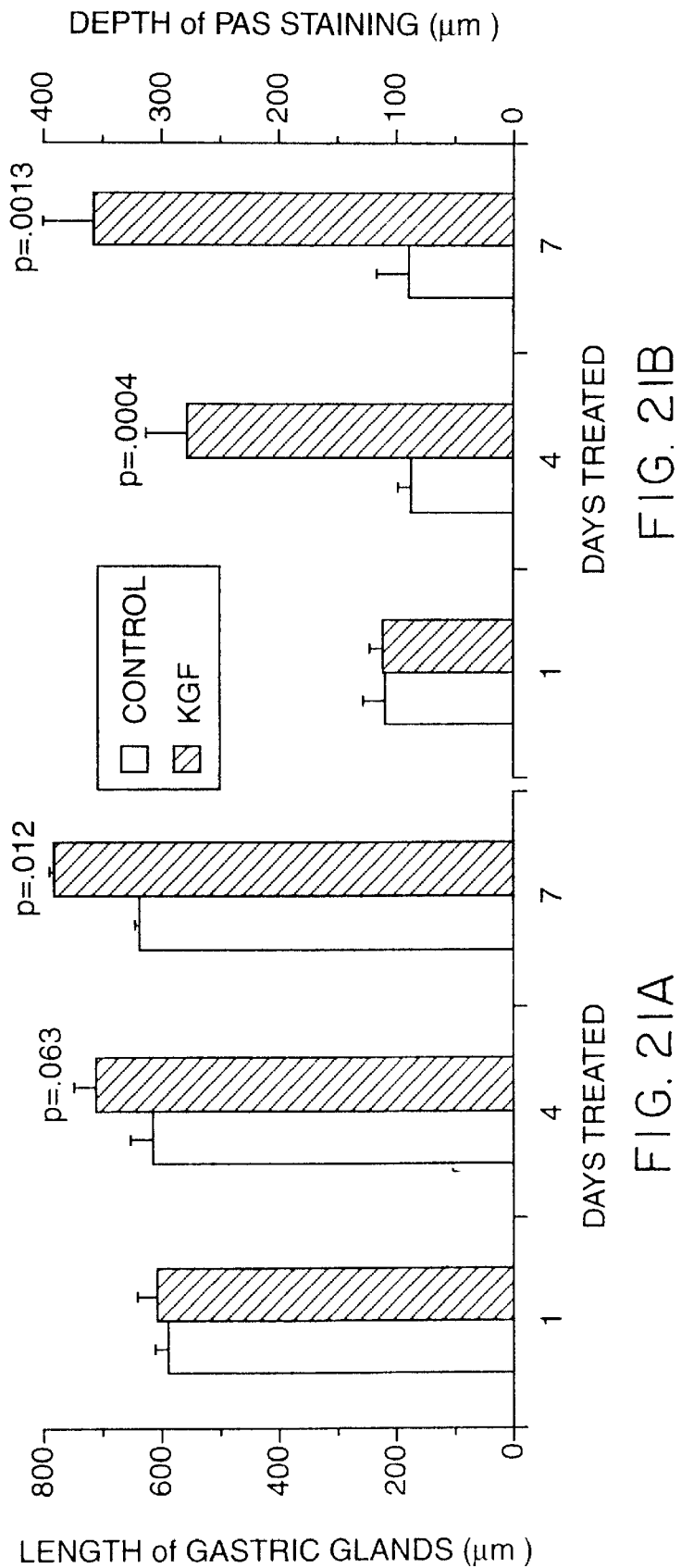
FIGS. 21A and 21B show the increased length of gastric glands and amount of mucus formation within the glandular stomach of rats treated with KGF from one to seven days.

The non-glandular foregut was significantly increased in weight at four and seven days of treatment. Histologically, the squamous epithelium of the non-glandular foregut was mildly (day four) to markedly (day seven) hyperplastic in KGF-treated animals. The proliferative epithelium changed abruptly at the cardia from the normal squamous epithelium of the esophagus to the proliferative epithelium of the treated foregut. The glandular gastric mucosa appeared normal histologically after one-day treatment. At four and seven days, an increased number of goblet cells was apparent histologically as cells with clear open cytoplasm. The animals treated with KGF for four and seven days showed a mild increase in the thickness of the mucosa (FIG. 21A). At seven days, the mucus neck cell layer was widened and displaced toward the serosal surface. PAS staining at four and seven days demonstrated striking increases in the number and size of PAS positive (mucin producing) goblet cells. BrdUstained sections further identified this layer as the dividing cell layer in the glandular stomach and showed an increase in proliferating cells with treatment. The thickness of the PAS positive layer of the luminal surface of the gastric mucosa was also markedly increased at four and seven days KGF treatment (FIG. 21B).

Figures 22A, 22B:
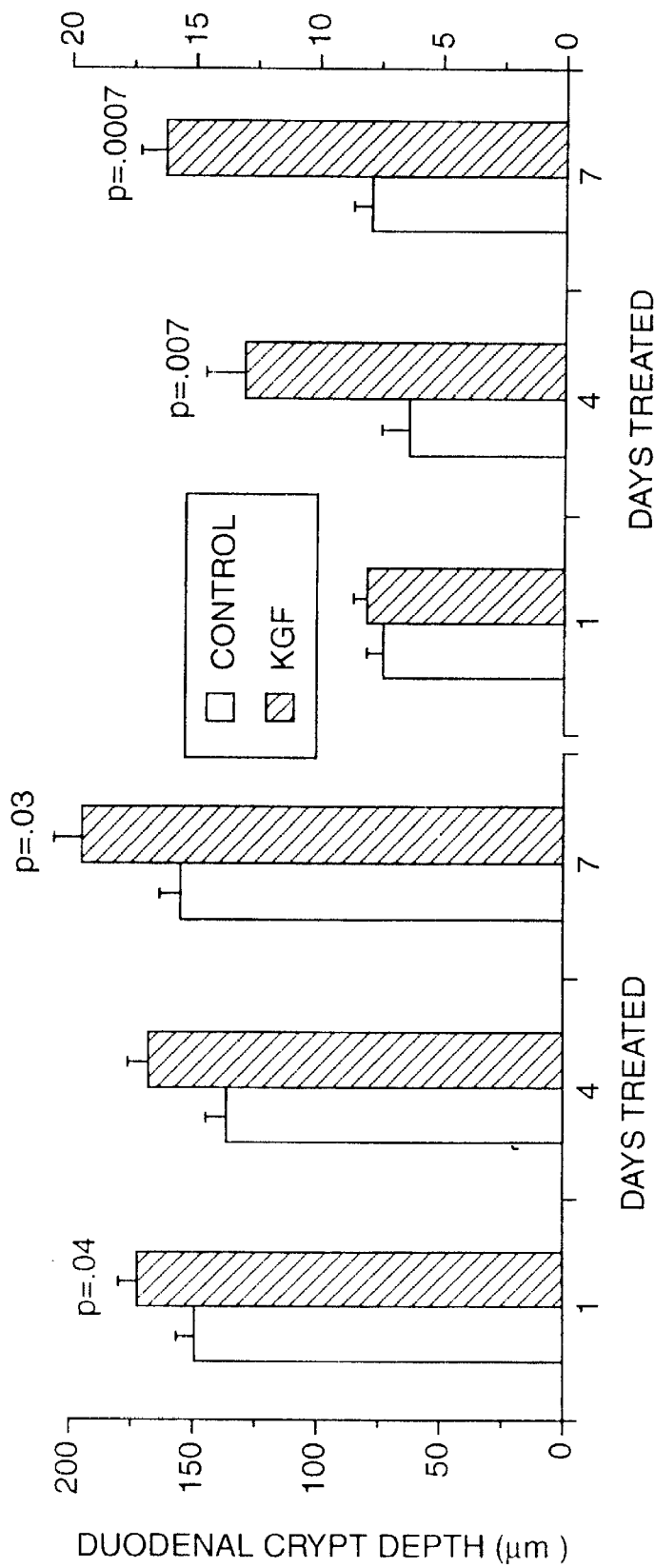
FIGS. 22A and 22B show the increased length of duodenal crypts and mucus production with the small intestine of rats treated from one to seven days with KGF.

The small intestine was grossly normal at all study points. PAS staining demonstrated an increased number of mucus producing goblet cells. This difference was significant at four and seven days (FIG. 22B). The villus height was not different at any time point but the crypt depth was significantly greater at one and seven days (FIG. 22A).

Figure 23:
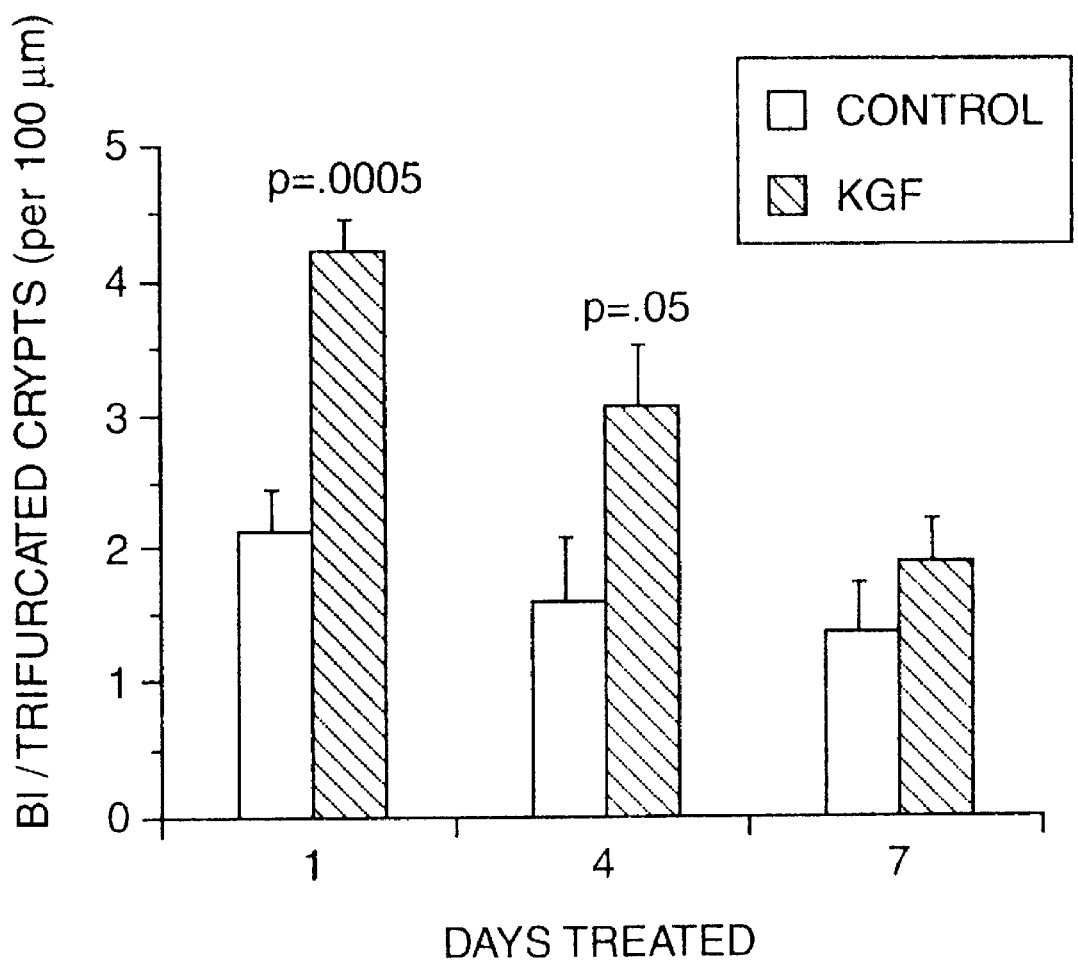
FIG. 23 shows an increase in hyperplastic crypts in the colon of rats treated from one to seven days with KGF.
Figure 24:
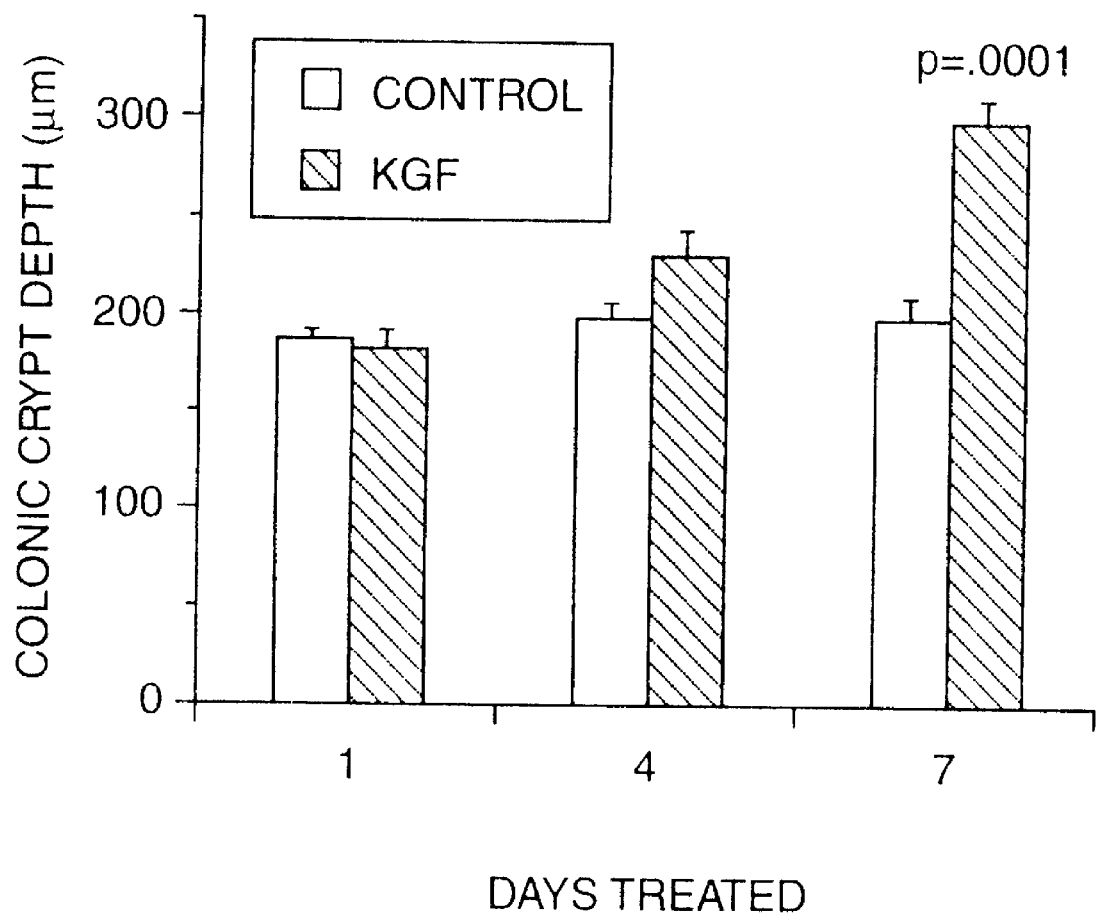
FIG. 24 shows an increase in colonic crypt depth in rats treated from one to seven days with KGF.

In seven-day treatment groups the colonic mucosa was thrown into rugal-like folds that greatly increased the overall surface area. Indicators of hyperplasia, bifurcated and trifurcated colonic crypts, were observed in all groups, including controls, but were most numerous and prominent in the short term treatment groups, e.g., days one and four, with the number of hyperplastic crypts decreasing with length of treatment (FIG. 23). Correspondingly, the depth of colonic crypts increased with treatment (FIG. 24).

PAS and Alcian blue staining indicted an increase in mucus producing goblet cells throughout the colon following KGF treatment. Additionally, the number of Alcian blue positive goblet cells at the luminal surface was increased at seven days in all treatment animals. Treatment animals as early as four days showed marked increases in PAS positive cells in the upper one-half and one-third of the colonic crypts.

These results demonstrate potent mitogenic and differentiation effects of KGF on epithelial tissues within the GI tract. It is apparent from BrdU labeling that KGF initiates proliferation of cells in the mucus neck layer of the gastric mucosa. These cells constitute the progenitor cells of the glandular stomach. Following division, cells from this layer migrate upwards, towards the gut lumen, to form surface cells or downward, towards the serosal surface, to become cells that occupy the gastric glands. (Toner et al., 1989, in *Gastrointestinal and Esophageal Pathology,* Churchill Livingstone, New York, N.Y., at pages 13–28). Additionally, KGF promotes selective differentiation of mucus neck cells to cells that move upward and that become goblet cells. The overall thickness of the gastric mucosa was increased at four and seven days of treatment. Similar effects were seen in the small and large intestines. KGF promoted increased cell division, resulting in elongated crypts, via stimulation of progenitor cells. KGF also induced differentiation of dividing crypt cells, as evidenced by increased mucus production and increased number of goblet cells in the villi or crypts.

While this invention has been described in relation to specific embodiments and examples, it should be understood that there is no intention for this description to be limiting. Thus, for instance, any form of KGF which substantially duplicates the biological properties of naturally occurring KGF can be employed to carry out the described uses. Such forms include purified naturally occurring KGF itself, KGF synthesized by chemical procedures, and KGF derived recombinantly using other expression systems besides the one illustrated above, as well as analogs, variants, chimeras, etc., based on the naturally occurring amino acid sequence. All such forms are intended for use in the practice of the present invention.

As those skilled in the art will also appreciate, a variety of host-vector systems may be utilized to express the KGF protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or other bacteria besides *E. coli* transformed with bacteriophage DNA, plasmid DNA, or cosmid DNA. The expression elements of these vectors vary in their strengths and specificities. Depending on the host-vector system utilized, any one of a number of suitable transcription and translation elements may be used.

Once the protein product of KGF cDNA expression has been isolated, purified and assayed for KGF activity, using methods such as described in this text or other procedures known to those skilled in the art, it may be formulated in a variety of pharmaceutical compositions. Typically, such compositions include a suitable, usually chemically defined, carrier or excipient for the therapeutic agent (KGF), and, depending on the intended form of administration, other ingredients as well. The composition can include aqueous carriers or consist of solid phase formulations in which KGF is incorporated into non-aqueous carriers such as collagens, hyaluronic acid, carboxymethyl cellulose and various polymers. The composition can be suitably formulated to be administered in a variety of ways, including by injection, orally, topically, intranasally, and by pulmonary delivery.

As the skilled practitioner will understand, the amount of KGF to be dosed will vary depending on the disease being treated and the route of administration, but may be effective in the range, for example, from 0.01 mg per kg of body weight to 500 mg per kg of body weight. It may be used once or administered repeatedly, depending on the disease and condition of the patient. It may be used in conjunction with other treatments, including, but not limited to, other cytokines and growth factors and other pharmaceutical preparations used to treat diseases of the skin, lungs, liver and gastrointestinal tract.

What is claimed is:

1. A method of treating a condition in a patient, said method comprising administering to such patient an effective amount of a keratinocyte growth factor product to stimulate the proliferation or differentiation of epithelial cells selected from the group consisting of hepatocytes, type II pneumocytes, mucin-producing goblet cells, and other epithelial cells and their progenitors contained within the liver, lung, and gastrointestinal tract.

2. The method of claim 1, wherein the keratinocyte growth factor product is formulated in a pharmaceutical composition.

3. The method of claim 2, wherein the pharmaceutical composition comprises an aqueous or a non-aqueous carrier.

4. The method of claim 3, wherein the non-aqueous carrier is selected from the group consisting of collagen and hyaluronic acid.

5. The method of claim 1, wherein the patient is administered a prophylactically or therapeutically effective amount of the keratinocyte growth factor product.

6. The method of claim 1, wherein the keratinocyte growth factor product is a naturally occurring keratinocyte growth factor, is a chemically synthesized keratinocyte growth factor, or is a recombinantly produced keratinocyte growth factor.

7. The method of claim 6, wherein the recombinantly produced keratinocyte growth factor comprises the amino acid sequence of a naturally occurring keratinocyte growth factor.

8. The method of claim 7, wherein the recombinantly produced keratinocyte growth factor is produced in bacterial cells.

9. The method of claim 8, wherein the bacterial cells are *E. coli*.

10. The method of claim 7, wherein the recombinant keratinocyte growth factor is administered by injection, orally, topically, intranasally or by pulmonary delivery.

11. The method of claim 10, wherein the recombinant keratinocyte growth factor is administered by injection.

12. The method of claim 10, wherein the recombinant keratinocyte growth factor is administered by pulmonary delivery.

13. The method of claim 7, wherein the recombinant keratinocyte growth factor is formulated in a pharmaceutical composition.

14. The method of claim 13, wherein the pharmaceutical composition comprises an aqueous or a non-aqueous carrier.

15. The method of claim 14, wherein the non-aqueous carrier is selected from the group consisting of collagen and hyaluronic acid.

16. A method for the treatment, including for the therapy or prevention, of a gastric ulcer, comprising administering an effective amount of a keratinocyte growth factor product to a patient in need thereof.

17. A method for the treatment, including for the therapy or prevention, of a duodenal ulcer, comprising administering an effective amount of a keratinocyte growth factor product to a patient in need thereof.

18. A method for the treatment, including for the therapy or prevention, of erosions of the stomach and esophagus, comprising administering an effective amount of a keratinocyte growth factor product to a patient in need thereof.

19. The method of claim 18, in which the illness being treated is erosive gastritis, esophagitis, or esophageal reflux.

20. A method for the treatment including for the therapy or prevention, of inflammatory bowel diseases, comprising administering an effective amount of a keratinocyte growth factor product to a patient in need thereof.

21. A method for the treatment, including for the therapy or preventions of radiation or chemotherapy-induced gut toxicity, comprising administering an effective amount of a keratinocyte growth factor product to a patient in need thereof.

22. A method for the treatment, including for the therapy or prevention, of necrosis of the respiratory epithelium caused by smoke inhalation, comprising administering an effective amount of a keratinocyte growth factor product to a patient in need thereof.

23. A method for the treatment, including for the therapy or prevention, of emphysema, comprising administering an effective amount of a keratinocyte growth factor product to a patient in need thereof.

24. A method for the treatment, including for the therapy or prevention, of pulmonary inflammation and fibrosis, comprising administering an effective amount of a keratinocyte growth factor product to a patient in need thereof.

* * * * *

UNITED STATES PATENT AND TRADEMARK OFFICE
CERTIFICATE OF CORRECTION

PATENT NO. : 5,824,643
DATED : October 20, 1998
INVENTOR(S) : Pierce et al.

It is certified that error appears in the above-identified patent and that said Letters Patent is hereby corrected as shown below:

Column 1,
Line 40, change "lung cell 8, brain cell 8," to -- lung cells, brain cells, --.

Column 4,
Line 44, change "injuroious" to -- injurious --.

Column 7,
Line 65, delete "35" after "glucose".

Column 8,
Line 63, insert -- reepithelialization -- after "of".

Column 12,
Line 36, insert -- on -- after "KGF".

Column 15,
Line 11, change "(p = 0.001)." to -- (p = 0.0001). --.

Signed and Sealed this

Third Day of August, 2004

JON W. DUDAS
*Acting Director of the United States Patent and Trademark Office*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

CGATTTGATT CTAGAAGGAG GAATAACATA TGGTTAACGC GTTGGAATTC GGTAC          55

( 2 ) INFORMATION FOR SEQ ID NO:2:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

CGAATTCCAA CGCGTTAACC ATATGTTATT CCTCCTTCTA GAATCAAAT          49

( 2 ) INFORMATION FOR SEQ ID NO:3:

( i ) SEQUENCE CHARACTERISTICS:
        ( A ) LENGTH: 164 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

GAAUACGAAU UCCUUGCUGU UUGGGCAGGA CAGUGAGCCA GGCAGACUGG UUGGCCUGCC          60

CUAUAUAAUU GGAGACCUUA CAUAUAUAUU CCCCAGCAUC CAUCUCCGUC ACAUUGAACA          120

GAGCCAGCAC UUCUGCAUUG GAGCUAUUUA UCCCCGAGUG GAUC          164

( 2 ) INFORMATION FOR SEQ ID NO:4:

( i ) SEQUENCE CHARACTERISTICS:
        ( A ) LENGTH: 191 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

GGGAGACAAG CUUGCAUGCC UGCAGGUCGA CUCUAGAGGA UCCACUCGGG GAUAAAUAGC          60

UCCAAUGCAG AAGUGCUGGC UCUGUUCAAU GUGACGGAGA UGGAUGCUGG GGAAUAUAUA          120

UGUAAGGUCU CCAAUUAUAU AGGGCAGGCC AACCAGUCUG CCUGGCUCAC UGUCCUGCCC          180

AAACAGCAAG G          191